United States Patent [19]

Miyazaki et al.

[11] Patent Number: 5,877,120
[45] Date of Patent: Mar. 2, 1999

[54] NICOTINIC ACID DERIVATIVES AND HERBICIDES

[75] Inventors: Masahiro Miyazaki; Sumio Yokota; Yoshihiro Ito; Nobuyuki Ohba; Nobuhide Wada, all of Iwata-gun; Shigehiko Tachikawa, Shizuoka; Takeshige Miyazawa, Ogasa-gun, all of Japan

[73] Assignees: Kumiai Chemical Industry Co., Ltd.; Ihara Chemical Industry Co., Ltd., both of Tokyo, Japan

[21] Appl. No.: 704,610

[22] PCT Filed: Mar. 22, 1994

[86] PCT No.: PCT/JP94/00453

§ 371 Date: Sep. 18, 1996

§ 102(e) Date: Sep. 18, 1996

[87] PCT Pub. No.: WO95/25730

PCT Pub. Date: Sep. 28, 1995

[51] Int. Cl.[6] .................. C07D 401/06; A01N 43/66
[52] U.S. Cl. .................. 504/239; 504/242; 504/243; 544/319; 544/326; 544/327; 544/328; 544/333
[58] Field of Search .................. 504/242, 243, 504/239; 544/319, 326, 327, 328, 333

[56] References Cited

U.S. PATENT DOCUMENTS

| 5,380,700 | 1/1995 | Miyazaki et al. | 504/239 |
| 5,385,880 | 1/1995 | Miyazaki et al. | 504/243 |
| 5,527,763 | 6/1996 | Miyazaki et al. | 504/242 |

FOREIGN PATENT DOCUMENTS 4-235967  8/1992  Japan .

*Primary Examiner*—John M. Ford
*Attorney, Agent, or Firm*—Oblon, Spivak, McClelland, Maier & Neustadt, P.C.

[57] ABSTRACT

A nicotinic acid derivative represented by general formula (I) or (II), a salt thereof, and a herbicide containing the same as the active ingredient, wherein A represents substituted phenyl, or 5- or 6- membered heterocycle, e.g., thienyl or pyridyl; R represents hydroxy, optionally substituted alkoxy or optionally substituted benzyloxy; $R^1$ and $R^2$ represent each independently alkoxy or halogen; $R^3$ and $R^4$ represent each independently hydrogen, hydroxy, cyano or alkoxycarbonyl, or they may be combined together to represent oxygen; X represents halogen, alkyl or alkoxy; n represents 0, 1 or 2; and Z represents methine or nitrogen. The compound and salts thereof can control annual or perennial weed growing on the land where various crops such as rice plant, wheat, cotton and corn grow for a wide period ranging from the pre-emergence to growth in a remarkably small dose.

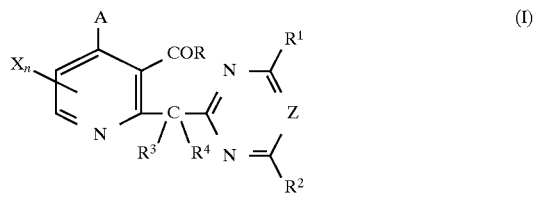

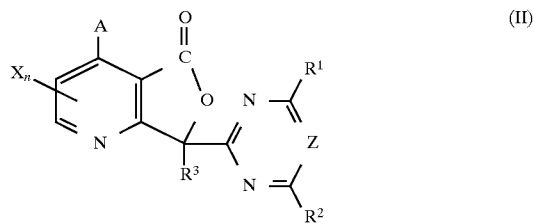

15 Claims, No Drawings

NICOTINIC ACID DERIVATIVES AND HERBICIDES

This application is a 371 of PCT/JP94/00453, filed Mar. 22, 1994.

TECHNICAL FIELD

The present invention relates to novel nicotinic acid derivatives or their salts, and herbicides containing them as active ingredients.

BACKGROUND ART

It is already known that nicotinic acid derivatives have herbicidal activities. For example, nicotinic acid derivatives represented by the formula

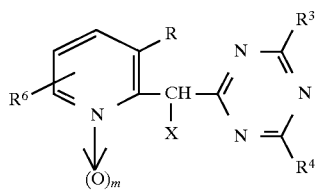

(Published Specification WO91/10653), heterocyclic derivatives represented by the formula

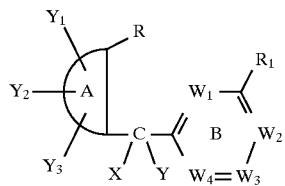

or

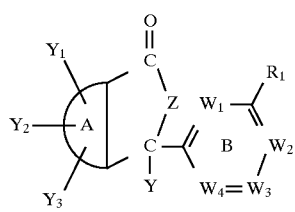

(Published Specification EP0461079) and nicotinic acid derivative represented by the formula

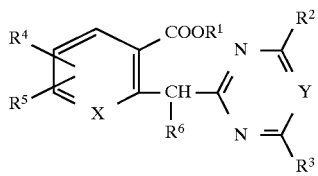

(Published Specification DE4026177) are known to have herbicidal activities.

The compounds disclosed in the above-mentioned Published Specifications are not necessarily satisfactory from the viewpoint of the herbicidal effects. A number of other herbicides have been developed and contributed to labor saving in farm work and to the improvement of the productivity. However, in their practical use, such herbicides also have various problems with respect to the herbicidal effects and the safety to crop plants.

Especially, in cultivation of barley and wheat, few herbicides can control gramineous weeds congeneric to barley and wheat, such as water foxtail, black grass and annual blue grass over a broad period of time from the pre-emergence season to the growing season of the weeds. Further, few herbicides have a broad selectivity between these herbicides and barley or wheat.

The present inventors have conducted an extensive research on nicotinic acid derivatives with the object of developing compounds which are not phytotoxic to valuable crop plants and have excellent herbicidal activities. As a result, they have found that the compounds of the present invention which are pyrimidine and triazine derivatives bonded to nicotinic acid substituted with a phenyl group or with a heterocyclic ring, exhibit excellent herbicidal effects against not only annual weeds but also perennial weeds, and are highly safe to crop plants. The present invention has been accomplished on the basis of this discovery.

DISCLOSURE OF THE INVENTION

Namely, the present invention relates to nicotinic acid derivatives represented by the general formula

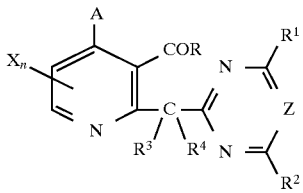  [I]

or

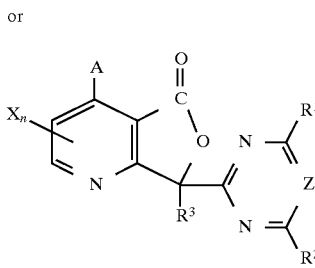  [II]

[wherein
A is one of the groups of the formulae

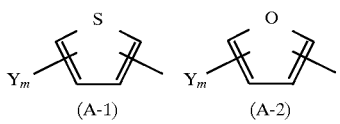

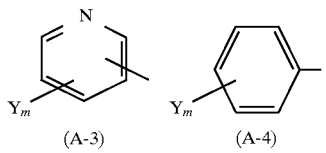

(wherein
Y is a halogen atom, a hydroxyl group, an optionally substituted alkoxy group, an alkenyloxy group, an alkynyloxy group, an optionally halogen-substituted alkyl group, an acyloxy group, a benzyloxy group or a nitro group, and m is 0 or an integer of from 1 to 3, provided that when m is 2 or 3, Y may be a combination of different groups), R is a hydroxyl group, an optionally substituted alkoxy group, an optionally substituted benzyloxy group, an alkenyloxy group, an alkynyloxy group, an optionally substituted phenoxy group, an optionally substituted phenylthio group, an alkylthio group, a 1-imidazolyl group, an isopropylideneaminoxy group or a group represented by the formula —NR⁵R⁶ (wherein each of $R^5$ and $R^6$ which may be the same or different, is a hydrogen atom, an alkyl group, an optionally substituted phenyl group, an alkylsulfonyl group or an optionally substituted phenylsulfonyl group, or $R^5$ and $R^6$ may form a ring together with the nitrogen atom) or the formula —ONR⁵R⁶ (wherein $R^5$ and $R^6$ are as defined above), each of $R^1$ and $R^2$ which may be the same or different, is a hydrogen atom, an alkoxy group, a halogen atom, an alkylamino group, a dialkylamino group, a halogen-substituted alkoxy group or an alkyl group, each of $R^3$ and $R^4$ which may be the same or different, is a hydrogen atom, a hydroxyl group, a cyano group or an alkoxycarbonyl group, or $R^3$ and $R^4$ may together represent an oxygen atom, X is a halogen atom, an alkyl group, an alkoxy group, an amino group, an alkylamino group, a dialkylamino group or an acylamino group, n is 0 or an integer of from 1 to 2, provided that when n is 2, X may be a combination of different groups, and Z is a methine group or a nitrogen atom] or their salt, and herbicides containing them as active ingredients. When

is a cyanomethylene group, the present invention covers their tautomers. A compound of the general formula [I] wherein R is a hydroxyl group, and $R^3$ and $R^4$ together represent an oxygen atom, corresponds to a compound of the general formula [II] wherein $R^3$ is a hydroxyl group.

In the general formulae [I], [II], (A—1), (A—2), (A—3) and (A—4), the optionally substituted alkoxy group as R is a linear or branched $C_{1-7}$ alkoxy group which may be substituted with an alkoxy group or a halogen atom, such as a methoxy group, an ethoxy group, an isopropoxy group, a t-butoxy group, a methoxyethoxy group or a chloroethoxy group. The optionally substituted benzyloxy group, the optionally substituted phenoxy group and the optionally substituted phenylthio group are respective groups which may be substituted with a halogen atom, an alkyl group, an alkoxy group, a nitro group or a cyano group.

The alkoxy group as $R^1$ or $R^2$ is a linear or branched $C_{1-7}$ alkoxy group such as a methoxy group, an ethoxy group or an isopropoxy group. The halogen atom is one of chlorine, bromine, fluorine and iodine atoms. The alkylamino group is a linear or branched $C_{1-3}$ alkylamino group such as a methylamino group or an ethylamino group. The dialkylamino group is a linear or branched $C_{1-3}$ dialkylamino group such as a dimethylamino group, a diethylamino group or a methylethylamino group. The halogen-substituted alkoxy group is a linear or branched $C_{1-7}$ alkoxy group partially or thoroughly substituted with the above-mentioned halogen atoms, such as a difluoromethoxy group or a trifluoromethoxy group. The alkyl group is a linear or branched $C_{1-7}$ alkyl group such as a methyl group or an ethyl group, an isopropyl group.

The alkoxycarbonyl group as $R^3$ or $R^4$ is a linear or branched $C_{1-7}$ alkoxycarbonyl group such as a methoxycarbonyl group, an ethoxycarbonyl group or an isopropoxycarbonyl group.

The alkyl group as $R^5$ or $R^6$ is similar to the groups described above for the alkyl group as the substituent $R^1$ or $R^2$. The optionally substituted phenyl group is, for example, a phenyl group which may be substituted with a halogen atom, an alkyl group, an alkoxy group or a nitro group. $R^5$ and $R^6$ may form, together with the nitrogen atom, a ring such as a pyrrolidinyl group or a piperazino group.

The halogen atom as Y is similar to those described above for the halogen atom as the substituent $R^1$ or $R^2$. The optionally substituted alkoxy group is a linear or branched $C_{1-7}$ alkoxy group which may be substituted with a halogen atom or an alkoxy group, such as a methoxy group, an ethoxy group or a difluoromethoxy group. The optionally halogen-substituted alkyl group is a linear or branched $C_{1-7}$ alkyl group which may be partially or thoroughly substituted with halogen atoms, such as a methyl group, an ethyl group, an isopropyl group, a trifluoromethyl group or a chloroethyl group.

The halogen atom, the alkyl group, the alkoxy group, the alkylamino group and the dialkylamino group as X are similar to the respective groups described above for the halogen atom, the alkyl group, the alkoxy group, the alkylamino group and the dialkylamino group as the substituent $R^1$ or $R^2$. The acylamino group is a $C_{1-7}$ acylamino group such as a formylamino group, an acetylamino group or a propionylamino group.

Now, specific examples of the compound of the present invention will be shown in Tables 1 to 3. The compound Nos. will be referred to in the subsequent description.

TABLE 1

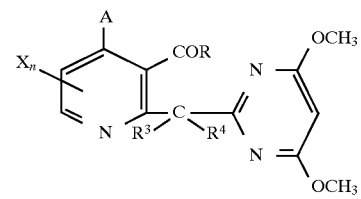

| Comp. No. | A | Xn | R | 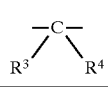 | Melting point (°C.) or refractive index ($n_D^{20}$) |
|---|---|---|---|---|---|
| 1 | S (pentagon) | H | OCH₃ | —CH(CN)— | 202~204 |
| 2 | " | 6-CH₃ | OCH₃ | —CH(CN)— | 197~200 |
| 3 | " | H | OCH₃ | —CO— | 129~132 |

TABLE 1-continued

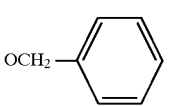

| Comp. No. | A | Xn | R | −C(R³)(R⁴)− | Melting point (°C.) or refractive index ($n_D^{20}$) |
|---|---|---|---|---|---|
| 4 | " | H | OCH₂-C₆H₅ | −CO− | Unmeasurable |
| 5 | " | H | OC₂H₅ | −CH(COOC₂H₅)− | |
| 6 | " | 5-CH₃ | OCH₃ | −CH(CN)− | |
| 7 | " | 6-Cl | OCH₃ | −CH(CN)− | |
| 8 | " | 6-NH₂ | OCH₃ | −CH(CN)− | |
| 9 | " | 6-NHCH₃ | OCH₃ | −CH(CN)− | |
| 10 | " | 6-N(CH₃)₂ | OCH₃ | −CH(CN)− | |
| 11 | " | 6-OCH₃ | OCH₃ | −CH(CN)− | |
| 12 | " | 5,6-(CH₃)₂ | OCH₃ | −CH(CN)− | |
| 13 | " | 6-NHCOCH₃ | OCH₃ | −CH(CN)− | |
| 14 | 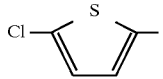 | H | OCH₃ | −CH(CN)− | 182~185 |
| 15 | " | H | OCH₃ | −CO− | 134~136 |
| 16 | " | H | OC₂H₅ | −CO− | 127~129 |
| 17 | " | H | OCH₂-C₆H₅ | −CO− | Unmeasurable |
| 18 | " | H | OCH₂CH=CH₂ | −CO− | 86.5~91 |
| 19 | " | H | OCH₂C≡CH | −CO− | |
| 20 | " | H | OCH₂-C₆H₄-CH₃ | −CO− | |
| 21 | " | H | O⁻Na⁺ | −CO− | |
| 22 | " | H | O⁻Na⁺ | −CH(OH)− | |
| 23 | 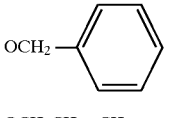 | H | OCH₃ | −CH(CN)− | 216~219 |
| 24 | 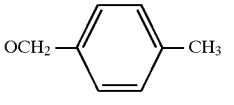 | H | OCH₃ | −CH(CN)− | |
| 25 | 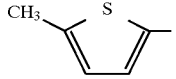 | H | OCH₃ | −CH(CN)− | |
| 26 | 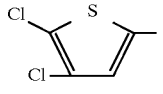 | H | OCH₃ | −CH(CN)− | |
| 27 | " | H | OCH₃ | −CO− | |

TABLE 1-continued
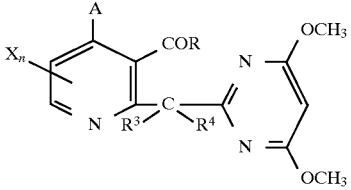
| Comp. No. | A | Xn | R | —C—(R³)(R⁴) | Melting point (°C.) or refractive index ($n_D^{20}$) |
|---|---|---|---|---|---|
| 28 | Br-[S] | H | OCH₃ | —CH(CN)— | |
| 29 | " | H | OCH₃ | —CO— | |
| 30 | CH₃O-[S] | H | OCH₃ | —CH(CN)— | |
| 31 | " | H | OCH₃ | —CO— | |
| 32 | NO₂-[S] | H | OCH₃ | —CH(CN)— | |
| 33 | " | H | OCH₃ | —CO— | |
| 34 | [S] | H | OCH₃ | —CH(CN)— | 227~230 |
| 35 | " | H | OCH₃ | —CO— | |
| 36 | CH₃-[S]-CH₃ | H | OCH₃ | —CH(CN)— | |
| 37 | [O] | H | OCH₃ | —CH(CN)— | 213~216 |
| 38 | " | H | OCH₃ | —CO— | 135~140 |
| 39 | " | H | OCH₂-[phenyl] | —CO— | |
| 40 | " | H | O⁻Na⁺ | —CO— | |
| 41 | CH₃-[O] | H | OCH₃ | —CH(CN)— | 207~211 |
| 42 | " | H | OCH₃ | —CO— | 122~123 |
| 43 | " | H | OC₂H₅ | —CO— | |
| 44 | Cl-[O] | H | OCH₃ | —CH(CN)— | |
| 45 | " | H | OCH₃ | —CO— | |

TABLE 1-continued
| Comp. No. | A | Xn | R | —C— R³  R⁴ | Melting point (°C.) or refractive index (n_D²⁰) |
|---|---|---|---|---|---|
| 46 | " | H | OCH₂—C₆H₅ | —CO— | |
| 47 | 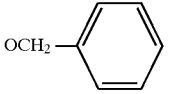 | H | OCH₃ | —CH(CN)— | |
| 48 | " | H | OCH₃ | —CO— | |
| 49 |  | H | OCH₃ | —CH(CN)— | >300 |
| 50 | " | H | OCH₃ | —CO— | |
| 51 | " | H | OC₂H₅ | —CO— | |
| 52 | " | H | OCH₂CH=CH₂ | —CO— | |
| 53 | 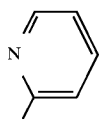 | H | OCH₃ | —CH(CN)— | >300 |
| 54 | " | H | OCH₃ | —CO— | |
| 55 | " | H | OCH₂—C₆H₅ | —CO— | |
| 56 |  | H | OCH₃ | —CH(CN)— | |
| 57 | " | H | OCH₃ | —CO— | |
| 58 |  | H | OCH₃ | —CH(CN)— | |
| 59 | " | H | OCH₃ | —CO— | |
| 60 | 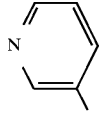 | H | OCH₃ | —CH(CN)— | 198~199 |
| 61 | " | H | OCH₃ | —CO— | 121~124 |

TABLE 1-continued

[Structure diagram showing: $X_n$ substituted pyridine ring with A, COR groups, connected via C(R³)(R⁴) to a pyrimidine ring with two OCH₃ groups]

| Comp. No. | A | Xn | R | $-\underset{R^4}{\overset{R^3}{\underset{|}{C}}}-$ | Melting point (°C.) or refractive index ($n_D^{20}$) |
|---|---|---|---|---|---|
| 62 | " | H | OCH₂—C₆H₅ | —CO— | 124~126 |
| 63 | " | H | O⁻Na⁺ | —CO— | |
| 64 | 4-Cl-C₆H₄— | H | OCH₃ | —CH(CN)— | 196~200 |
| 65 | " | H | OCH₃ | —CO— | 156~158 |
| 66 | " | H | OCH₂—C₆H₄—CH₃ | —CO— | |
| 67 | 3-Cl-C₆H₄— | H | OCH₃ | —CH(CN)— | 160~163 |
| 68 | " | H | OCH₃ | —CO— | 122~123 |
| 69 | 2-Cl-C₆H₄— | H | OCH₃ | —CH(CN)— | 187~191 |
| 70 | " | H | OCH₃ | —CO— | 134~137 |
| 71 | 4-F-C₆H₄— | H | OCH₃ | —CH(CN)— | 200~204 |
| 72 | " | H | OCH₃ | —CO— | 158~159 |
| 73 | 3-F-C₆H₄— | H | OCH₃ | —CH(CN)— | |
| 74 | " | H | OCH₃ | —CO— | |
| 75 | 4-Br-C₆H₄— | H | OCH₃ | —CH(CN)— | |
| 76 | " | H | OCH₃ | —CO— | |
| 77 | 4-CH₃O-C₆H₄— | H | OCH₃ | —CH(CN)— | 164~166 |

TABLE 1-continued

| Comp. No. | A | Xn | R | $\underset{R^3\phantom{xx}R^4}{-\overset{\displaystyle |}{\underset{\displaystyle |}{C}}-}$ | Melting point (°C.) or refractive index ($n_D^{20}$) |
|---|---|---|---|---|---|
| 78 | " | H | OCH$_3$ | —CO— | 166~169 |
| 79 | 3-CH$_3$O-phenyl | H | OCH$_3$ | —CH(CN)— | |
| 80 | " | H | OCH$_3$ | —CO— | |
| 81 | 4-CH$_3$-phenyl | H | OCH$_3$ | —CH(CN)— | 201~203.5 |
| 82 | " | H | OCH$_3$ | —CO— | 155~159 |
| 83 | 3-CH$_3$-phenyl | H | OCH$_3$ | —CH(CN)— | |
| 84 | " | H | OCH$_3$ | —CO— | |
| 85 | 3,4-di-CH$_3$-phenyl | H | OCH$_3$ | —CH(CN)— | 180~183 |
| 86 | " | H | OCH$_3$ | —CO— | 140~143 |
| 87 | 3-CF$_3$-phenyl | H | OCH$_3$ | —CH(CN)— | |
| 88 | " | H | OCH$_3$ | —CO— | |
| 89 | 4-CHF$_2$O-phenyl | H | OCH$_3$ | —CH(CN)— | |
| 90 | " | H | OCH$_3$ | —CO— | |
| 91 | 3-CHF$_2$O-phenyl | H | OCH$_3$ | —CH(CN)— | |
| 92 | " | H | OCH$_3$ | —CO— | |

TABLE 1-continued

| Comp. No. | A | Xn | R | -C- R³ R⁴ | Melting point (°C.) or refractive index ($n_D^{20}$) |
|---|---|---|---|---|---|
| 93 | 3,4-diCl-phenyl | H | $OCH_3$ | $-CH(CN)-$ | |
| 94 | " | H | $OCH_3$ | $-CO-$ | |
| 95 | phenyl | H | $OCH_3$ | $-C(OH)(CN)-$ | 126~129 |
| 96 | 2-thienyl | H | $O^-Na^+$ | $-CO-$ | >300 |
| 97 | 4-Cl-phenyl | H | $O^-Na^+$ | $-CO-$ | 263~267 |
| 98 | 5-Cl-2-thienyl | H | $OC_3H_7$ | $-CO-$ | 91~94 |
| 99 | " | H | $OC_3H_7$-iso | $-CO-$ | 112~115 |
| 100 | " | H | imidazolyl | $-CO-$ | 160~163 |
| 101 | " | H | $-N(C_2H_5)_2$ | $-CO-$ | 130~133 |
| 102 | " | H | $OC_2H_5$ | $-C(OH)(COOC_2H_5)-$ | 109~112 |
| 103 | " | H | $OC_2H_5$ | $-CHCOOC_2H_5$ | 127~132 |
| 104 | 4-$NO_2$-phenyl | H | $OCH_3$ | $-CH(CN)-$ | 229~235 |
| 105 | phenyl | H | $OC_2H_5$ | $-CO-$ | 130~133 |
| 106 | " | H | $OC_3H_7$ | $-CO-$ | 88~90 |
| 107 | " | H | $OC_3H_7$-iso | $-CO-$ | 139~141 |
| 108 | " | H | $OC_4H_9$ | $-CO-$ | 1.5629 |

TABLE 1-continued
| Comp. No. | A | Xn | R | —C— R³  R⁴ | Melting point (°C.) or refractive index (n_D²⁰) |
|---|---|---|---|---|---|
| 109 | " | H | -S-C₆H₅ | —CO— | |
| 110 | " | H | OCH₂CH₂OCH₃ | —CO— | 99~100 |
| 111 | " | H | OC₄H₉-t | —CO— | |
| 112 | " | H | —N(imidazole) | —CO— | 126~128 |
| 113 | " | H | SCH₃ | —CO— | |
| 114 | " | H | SC₂H₅ | —CO— | |
| 115 | " | H | SC₃H₇ | —CO— | |
| 116 | " | H | SC₃H₇-iso | —CO— | |
| 117 | " | H | N(C₂H₅)₂ | —CO— | |
| 118 | " | H | —O—C₆H₅ | —CO— | |
| 119 | " | H | —O—C₆H₄—Cl | —CO— | |
| 120 | " | H | OCH₂—C₆H₄—Cl | —CO— | 126~127 |
| 121 | " | H | OCH₂—C₆H₄—OCH₃ | —CO— | |
| 122 | " | H | —O—C₆H₄—CH₃ | —CO— | |
| 123 | " | H | OCH₂—C₆H₄—NO₂ | —CO— | |
| 124 | " | H | OCH₂—C₆H₄—CN | —CO— | |
| 125 | " | H | OCH₂—C₆H₄—CH₃ | —CO— | |
| 126 | " | H | OCH₂CH=CH₂ | —CO— | 70~71 |

TABLE 1-continued

| Comp. No. | A | Xn | R | $\underset{R^3 \quad R^4}{-\overset{\mid}{\underset{\mid}{C}}-}$ | Melting point (°C.) or refractive index ($n_D^{20}$) |
|---|---|---|---|---|---|
| 127 | " | H | OCH$_2$C≡CH | —CO— | |
| 128 | " | H | OC$_4$H$_9$-s | —CO— | |
| 129 | " | H | OC$_4$H$_9$-iso | —CO— | |
| 130 | " | H | O—N=C(CH$_3$)$_2$ | —CO— | |
| 131 | " | H | 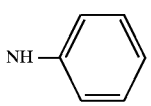 | —CO— | |
| 132 | " | H | NHSO$_2$CH$_3$ | —CO— | |
| 133 | " | H | 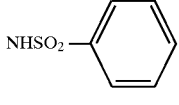 | —CO— | |
| 134 | " | H | OCH$_2$CH$_2$Cl | —CO— | 89~90 |
| 135 | 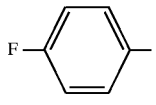 | H | OC$_2$H$_5$ | —CO— | 116~119 |
| 136 | " | H | OC$_3$H$_7$ | —CO— | 90~93 |
| 137 | " | H | OC$_3$H$_7$-iso | —CO— | 141~142 |
| 138 | " | H | OCH$_2$CH=CH$_2$ | —CO— | 91~92 |
| 139 | " | H | 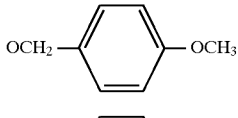 | —CO— | |
| 140 | " | H | 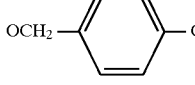 | —CO— | |
| 141 | " | H | NHSO$_2$CH$_3$ | —CO— | |
| 142 | " | H |  | —CO— | |
| 143 | " | H | SC$_2$H$_5$ | —CO— | |
| 144 | " | H | N(C$_2$H$_5$)$_2$ | —CO— | 185~188 |
| 145 | " | H | ON=C(CH$_3$)$_2$ | —CO— | 193~196 |
| 146 | " | H | ON(C$_2$H$_5$)$_2$ | —CO— | 143~145 |
| 147 | 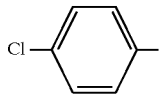 | H | OC$_2$H$_5$ | —CO— | 106~108 |
| 148 | " | H | OC$_3$H$_7$ | —CO— | 89~91 |
| 149 | " | H | OC$_3$H$_7$-iso | —CO— | 112~115 |
| 150 | " | H | OCH$_2$CH=CH$_2$ | —CO— | 110~112 |
| 151 | " | H | SCH$_3$ | —CO— | 211~214 |
| 152 | " | H | SC$_2$H$_5$ | —CO— | 205~207 |
| 153 | " | H | SC$_3$H$_7$ | —CO— | 200~201 |

TABLE 1-continued

| Comp. No. | A | Xn | R | —C—<br>R³  R⁴ | Melting point (°C.) or refractive index ($n_D^{20}$) |
|---|---|---|---|---|---|
| 154 | " | H | —O—(phenyl) | —CO— | |
| 155 | " | H | O—N=C(CH₃)₂ | —CO— | |
| 156 | " | H | OCH₂—(phenyl) | —CO— | 143~146 |
| 157 | " | H | OCH₂—(phenyl)—CH₃ | —CO— | |
| 158 | " | H | OCH₂CH=CH₂ | —CO— | |
| 159 | " | H | OCH₂C≡CH | —CO— | |
| 160 | CH₃O—(phenyl)— | H | OC₂H₅ | —CO— | 119~121 |
| 161 | " | H | OC₃H₇ | —CO— | 68~70 |
| 162 | " | H | OC₃H₇-iso | —CO— | 98~100 |
| 163 | " | H | OC₄H₉ | —CO— | |
| 164 | " | H | OCH₂CH=CH₂ | —CO— | |
| 165 | " | H | OCH₂C≡CH | —CO— | |
| 166 | " | H | OCH₂—(phenyl) | —CO— | |
| 167 | " | H | —O—(phenyl) | —CO— | |
| 168 | " | H | —N(imidazole) | —CO— | |
| 169 | " | H | SC₂H₅ | —CO— | |
| 170 | " | H | NHSO₂CH₃ | —CO— | |
| 171 | CH₃—(phenyl)— | H | OC₂H₅ | —CO— | 103~105 |
| 172 | " | H | OC₃H₇ | —CO— | 133~136 |
| 173 | " | H | OC₃H₇-iso | —CO— | |
| 174 | " | H | OC₄H₉ | —CO— | |
| 175 | " | H | OCH₂CH=CH₂ | —CO— | |

TABLE 1-continued
| Comp. No. | A | Xn | R | —C—<br>R³  R⁴ | Melting point (°C.) or refractive index (n_D^20) |
|---|---|---|---|---|---|
| 176 | " | H | OCH₂C≡CH | —CO— | |
| 177 | " | H | OCH₂—C₆H₅ | —CO— | |
| 178 | " | H | O—C₆H₅ | —CO— | |
| 179 | " | H | —N(imidazole) | —CO— | |
| 180 | " | H | SC₂H₅ | —CO— | |
| 181 | " | H | NHSO₂CH₃ | —CO— | |
| 182 | CH₂=CHCH₂O—C₆H₄— | H | OC₂H₅ | —CO— | |
| 183 | CH≡CCH₂O—C₆H₄— | H | OC₂H₅ | —CO— | |
| 184 | HO—C₆H₄— | H | OC₂H₅ | —CO— | |
| 185 | C₆H₅CH₂O—C₆H₄— | H | OC₂H₅ | —CO— | |
| 186 | 3,4-Cl₂—C₆H₃— | H | OC₂H₅ | —CO— | |
| 187 | 2-Cl-5-CH₃O—C₆H₃— | H | OC₂H₅ | —CO— | |
| 188 | CH₃COO—C₆H₄— | H | OC₂H₅ | —CO— | |

TABLE 1-continued

| Comp. No. | A | Xn | R | —C— R³ R⁴ | Melting point (°C.) or refractive index ($n_D^{20}$) |
|---|---|---|---|---|---|
| 189 | 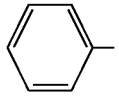 | H | $OC_2H_5$ |  CHCOOC$_2$H$_5$ | |
| 190 | " | H | $OC_2H_5$ |  C(OH)COOC$_2$H$_5$ | |

TABLE 2

| Comp. No. | A | Xn | R | —C— R³ R⁴ | Z | R¹ | R² | Melting point (°C.) or refractive index ($n_D^{20}$) |
|---|---|---|---|---|---|---|---|---|
| 191 | 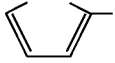 | H | $OCH_3$ | CH(CN) | CH | $CH_3$ | $CH_3$ | |
| 192 | " | H | $OCH_3$ | CO | CH | $CH_3$ | $CH_3$ | |
| 193 | " | H | $OCH_3$ | CH(CN) | N | $OCH_3$ | $OCH_3$ | |
| 194 | " | H | $OCH_3$ | CO | N | $OCH_3$ | $OCH_3$ | |
| 195 | 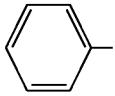 | H | $OCH_3$ | CH(CN) | CH | $CH_3$ | $CH_3$ | |
| 196 | " | H | $OCH_3$ | CO | CH | $CH_3$ | $CH_3$ | |
| 197 | " | H | $OCH_3$ | CH(CN) | N | $CH_3$ | $CH_3$ | |
| 198 | " | H | $OCH_3$ | CO | N | $CH_3$ | $CH_3$ | |
| 199 | " | H | $OCH_3$ | CH(CN) | N | $OCH_3$ | $OCH_3$ | |
| 200 | " | H | $OCH_3$ | CO | N | $OCH_3$ | $OCH_3$ | |
| 201 | " | H | $OCH_3$ | CH(CN) | CH | $CH_3$ | $OCH_3$ | |
| 202 | " | H | $OCH_3$ | CO | CH | $CH_3$ | $OCH_3$ | |
| 203 | " | H | $OCH_3$ | CH(CN) | CH | $N(CH_3)_2$ | $OCH_3$ | |
| 204 | " | H | $OCH_3$ | CO | CH | $N(CH_3)_2$ | $OCH_3$ | |
| 205 | " | H | $OC_2H_5$ | CHCOOC$_2$H$_5$ | CH | $OCH_3$ | Cl | |
| 206 | " | H | $OC_2H_5$ | CHCOOC$_2$H$_5$ | N | $OCH_3$ | Cl | |
| 207 | " | H | $OC_2H_5$ | CO | CH | $OCHF_2$ | $OCH_3$ | |

TABLE 3

[Structure: pyridine ring with substituents Xn, A, and C(=O)O-pyrimidine group with R1, R2, R3, Z substituents]

| Comp. No. | A | Xn | R¹ | R² | R³ | Z | Melting point (°C.) or refractive index ($n_D^{20}$) |
|---|---|---|---|---|---|---|---|
| 208 | (thiophene-2-yl) | H | OCH₃ | OCH₃ | CN | CH | 187~188.5 |
| 209 | " | H | OCH₃ | OCH₃ | OH | CH | 218~221 |
| 210 | " | H | OCH₃ | OCH₃ | H | CH | 120~123 |
| 211 | " | H | OCH₃ | OCH₃ | CN | N | |
| 212 | " | H | OCH₃ | OCH₃ | OH | N | |
| 213 | " | " | H | OCH₃ | OCH₃ | H | N | |
| 214 | " | H | CH₃ | CH₃ | CN | CH | |
| 215 | " | H | CH₃ | CH₃ | OH | CH | |
| 216 | " | H | CH₃ | CH₃ | H | CH | |
| 217 | (5-Cl-thiophene-2-yl) | H | OCH₃ | OCH₃ | CN | CH | 183~184 |
| 218 | " | H | OCH₃ | OCH₃ | OH | CH | 207~209 |
| 219 | (4-Cl-thiophene-2-yl) | H | OCH₃ | OCH₃ | CN | CH | |
| 220 | " | H | OCH₃ | OCH₃ | OH | CH | |
| 221 | (5-CH₃-thiophene-2-yl) | H | OCH₃ | OCH₃ | CN | CH | |
| 222 | " | H | OCH₃ | OCH₃ | OH | CH | |
| 223 | (4,5-diCl-thiophene-2-yl) | H | OCH₃ | OCH₃ | CN | CH | |
| 224 | " | H | OCH₃ | OCH₃ | OH | CH | |
| 225 | (thiophene-3-yl) | H | OCH₃ | OCH₃ | CN | CH | |
| 226 | " | H | OCH₃ | OCH₃ | OH | CH | |
| 227 | " | H | OCH₃ | OCH₃ | H | CH | |
| 228 | (furan-2-yl) | H | OCH₃ | OCH₃ | CN | CH | 215~218 |
| 229 | " | H | OCH₃ | OCH₃ | OH | CH | 198~204 |
| 230 | " | H | OCH₃ | OCH₃ | H | CH | |

TABLE 3-continued

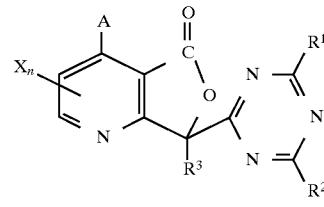

| Comp. No. | A | Xn | R¹ | R² | R³ | Z | Melting point (°C.) or refractive index ($n_D^{20}$) |
|---|---|---|---|---|---|---|---|
| 231 | 5-methyl-furan-2-yl | H | OCH₃ | OCH₃ | CN | CH | |
| 232 | " | H | OCH₃ | OCH₃ | OH | CH | 215~220 |
| 233 | pyridin-3-yl | H | OCH₃ | OCH₃ | CN | CH | 215~217 |
| 234 | " | H | OCH₃ | OCH₃ | OH | CH | 207~211 |
| 235 | pyridin-4-yl | H | OCH₃ | OCH₃ | CN | CH | 180~185 |
| 236 | " | H | OCH₃ | OCH₃ | OH | CH | 203~205 |
| 237 | 2-methyl-pyridin-4-yl (with additional CH₃) | H | OCH₃ | OCH₃ | CN | CH | |
| 238 | " | H | OCH₃ | OCH₃ | OH | CH | |
| 239 | 5-chloro-furan-2-yl | H | OCH₃ | OCH₃ | CN | CH | |
| 240 | " | H | OCH₃ | OCH₃ | OH | CH | |
| 241 | " | H | OCH₃ | OCH₃ | H | CH | |
| 242 | 5-bromo-thiophen-2-yl | H | OCH₃ | OCH₃ | CN | CH | |
| 243 | " | H | OCH₃ | OCH₃ | OH | CH | |
| 244 | phenyl | H | OCH₃ | OCH₃ | CN | CH | 196~198 |
| 245 | " | H | OCH₃ | OCH₃ | OH | CH | 189~192 |
| 246 | " | H | OCH₃ | OCH₃ | H | CH | 151~153.5 |
| 247 | 4-chlorophenyl | H | OCH₃ | OCH₃ | CN | CH | |
| 248 | " | H | OCH₃ | OCH₃ | OH | CH | 228~231 |
| 249 | " | H | OCH₃ | OCH₃ | H | CH | |

TABLE 3-continued

| Comp. No. | A | Xn | R¹ | R² | R³ | Z | Melting point (°C.) or refractive index ($n_D^{20}$) |
|---|---|---|---|---|---|---|---|
| 250 | 4-F-C₆H₄- | H | OCH₃ | OCH₃ | CN | CH | |
| 251 | " | H | OCH₃ | OCH₃ | OH | CH | 217~221 |
| 252 | 3-Cl-C₆H₄- | H | OCH₃ | OCH₃ | CN | CH | |
| 253 | " | H | OCH₃ | OCH₃ | OH | CH | 223~226 |
| 254 | 2-Cl-C₆H₄- | H | OCH₃ | OCH₃ | CN | CH | |
| 255 | " | H | OCH₃ | OCH₃ | OH | CH | 221~226 |
| 256 | 3-F-C₆H₄- | H | OCH₃ | OCH₃ | CN | CH | |
| 257 | " | H | OCH₃ | OCH₃ | OH | CH | |
| 258 | 4-CH₃O-C₆H₄- | H | OCH₃ | OCH₃ | CN | CH | |
| 259 | " | H | OCH₃ | OCH₃ | OH | CH | 192~195 |
| 260 | 3-CH₃O-C₆H₄- | H | OCH₃ | OCH₃ | CN | CH | |
| 261 | " | H | OCH₃ | OCH₃ | OH | CH | |
| 262 | 4-CHF₂O-C₆H₄- | H | OCH₃ | OCH₃ | CN | CH | |
| 263 | " | H | OCH₃ | OCH₃ | OH | CH | |
| 264 | 3-CHF₂O-C₆H₄- | H | OCH₃ | OCH₃ | CN | CH | |

TABLE 3-continued

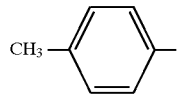

| Comp. No. | A | Xn | R¹ | R² | R³ | Z | Melting point (°C.) or refractive index ($n_D^{20}$) |
|---|---|---|---|---|---|---|---|
| 265 | " | H | OCH₃ | OCH₃ | OH | CH | |
| 266 | CH₃—⟨phenyl⟩— | H | OCH₃ | OCH₃ | CN | CH | |
| 267 | " | H | OCH₃ | OCH₃ | OH | CH | 190~193 |
| 268 | 2,3-(CH₃)₂-⟨phenyl⟩— | H | OCH₃ | OCH₃ | CN | CH | |
| 269 | " | H | OCH₃ | OCH₃ | OH | CH | 213~216 |
| 270 | 3,4-Cl₂-⟨phenyl⟩— | H | OCH₃ | OCH₃ | CN | CH | |
| 271 | " | H | OCH₃ | OCH₃ | OH | CH | |
| 272 | Cl-⟨thienyl⟩— | H | OCH₃ | OCH₃ | COOC₂H₅ | CH | 150~156 |
| 273 | O₂N-⟨phenyl⟩— | H | OCH₃ | OCH₃ | OH | CH | 249~259 |
| 274 | ⟨phenyl⟩— | H | OCH₃ | OCH₃ | COOC₂H₅ | CH | |

The compounds represented by the general formulae [I] and [II] of the present invention can be prepared, for example, in accordance with the following processes <1> to <10>. However, processes for producing them are by no means restricted to these processes.

Process <1>

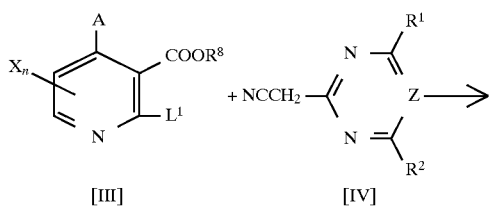

-continued

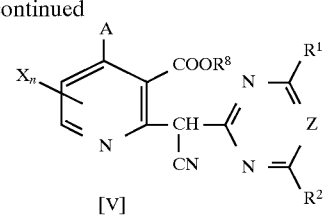

(wherein A, X, n, Z, R¹ and R² are as defined above, L¹ is a halogen atom, and R⁸ is an alkyl group.)

A compound represented by the general formula [V] can be prepared by reaction of a compound represented by the general formula [III] with a compound represented by the general formula [IV] in the presence of at least twice the equivalent amount of a base in an ethereal solvent such as tetrahydrofuran or in a non-polar solvent such as N,N-dimethylformamide at a temperature within a range of from room temperature to the boiling point of the solvent for from 1 to 4 hours, and subsequent acidification.

As the base, an alkali metal hydroxide such as sodium hydroxide or potassium hydroxide, an alkali metal hydride such as sodium hydride or potassium hydride, or an alkali metal alkoxide such as potassium t-butoxide, may be used.

A compound represented by the general formula [III] can be prepared in accordance with the following method disclosed in J. Org. Chem. vol. 41, p. 2066 (1976); and Aust. J. Chem. vol. 36, p. 1441 (1983).

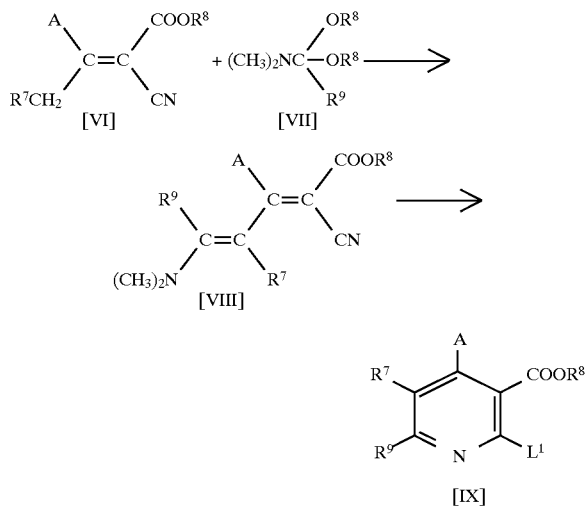

(wherein each of $R^7$ and $R^9$ which may be the same or different, is a hydrogen atom, an alkyl group or an alkoxy group, and $R^8$, $L^1$ and A are as defined above.)

Namely, a compound represented by the general formula [VIII] can be prepared by heating a compound presented by the general formula [VI] and an acetal compound represented by the general formula [VII] in the presence or absence of an inorganic or organic base in an alcoholic solvent such as methanol or ethanol, an ethereal solvent such as tetrahydrofuran, an aprotic polar solvent such as N,N-dimethylformamide or an acetonitrile solvent for from 0.1 to 10 hours.

A compound represented by the general formula [IX] can be prepared by reacting a compound represented by the general formula [VIII] in acetic acid or in an inert solvent such as dichloroethane or toluene, with hydrogen bromide or hydrogen chloride gas at a temperature within a range of from 0° C. to the boiling point of the solvent, preferably from 10° C. to 50° C.

A compound represented by the general formula [IV] can be prepared by the following method.

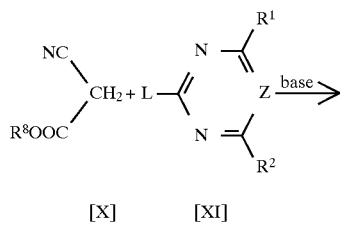

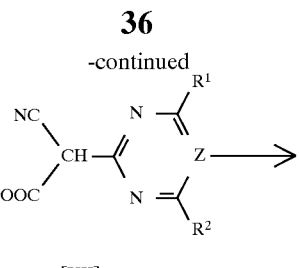

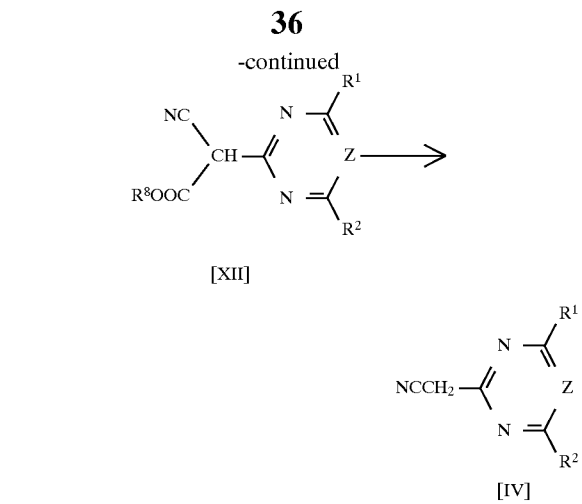

(wherein $R^1$, $R^2$, $R^8$ and Z are as defined above, L is an eliminable group such as a halogen atom or an alkylsulfonyl group.)

Namely, a compound represented by the general formula [XII] can be prepared by reacting a cyanoacetic ester represented by the general formula [X] with a compound represented by the general formula [XI] in the presence of at least the equivalent amount of a base in a suitable solvent at a temperature within a range of from room temperature to the boiling point of the solvent for from 1 to 24 hours.

As the base, an alkali metal such as metal lithium, metal sodium or metal potassium, an organic lithium reagent such as n-butyl lithium or lithium diisopropylamide (LDA), an alkali metal hydride such as sodium hydride or potassium hydride, an alkali metal alkoxide such as potassium t-butoxide, an alkali metal carbonate such as sodium carbonate or potassium carbonate, or an alkali metal hydroxide such as sodium hydroxide or potassium hydroxide, may be used.

As the solvent, a hydrocarbon solvent such as toluene or xylene, a halogenated hydrocarbon solvent such as dichloromethane or chloroform, an ethereal solvent such as diethyl ether, tetrahydrofuran or 1,4-dioxane, an ester solvent such as ethyl acetate, a ketone solvent such as acetone, an aprotic polar solvent such as N,N-dimethylformamide or dimethyl sulfoxide, or acetonitrile, may, for example, be used.

A compound represented by the general formula [IV] can be prepared by reacting a compound represented by the general formula [XII] with twice the equivalent amount of water and a catalytic amount of an inorganic salt such as sodium chloride in an aprotic polar solvent such as dimethyl sulfoxide at 150° C. for from 1 to 5 hours.

Process <2>

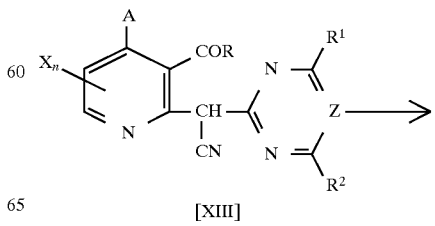

-continued

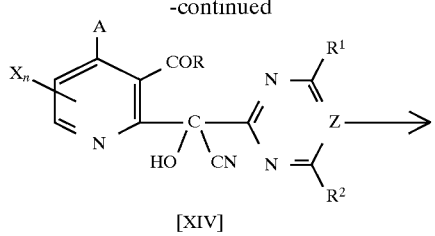

[XIV]

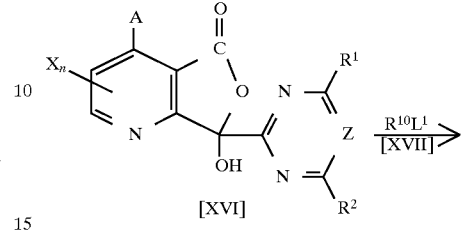

[XV]

(wherein A, X, n, R, R¹, R² and Z are as defined above.)

A compound represented by the general formula [XV] can be prepared by reacting a compound represented by the general formula [XIII] with an organic peroxide such as m-chloroperbenzoic acid in a halogenated hydrocarbon solvent such as dichloromethane or chloroform at room temperature for from 0.5 to 24 hours.

A compound represented by the general formula [XV] is sometimes obtained in a mixture with a compound represented by the general formula [XIV]. In this case, it can be isolated and purified by recrystallization from a suitable solvent or silica gel column chromatography.

Process <3>

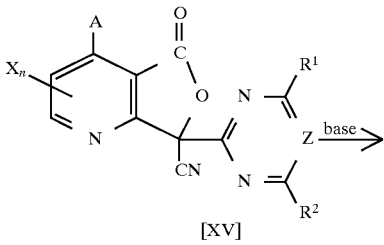

[XV]

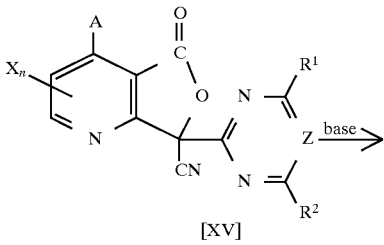

[XVI]

(wherein A, X, n, R, R¹, R² and Z are as defined above.)

A compound represented by the general formula [XVI] can be prepared by reaction of a compound represented by the general formula [XV] in the presence of at least the equivalent amount of a base in water or in a suitable hydrous solvent at a temperature within a range of from room temperature to the boiling point of the solvent for from 0.5 to 24 hours, the subsequent acidification.

As the base, an alkali metal hydroxide such as sodium hydroxide or potassium hydroxide may, for example, be used.

As the solvent, a hydrocarbon solvent such as toluene, an alcoholic solvent such as methanol or ethanol, an ethereal solvent such as ethyl ether or tetrahydrofuran, a ketone solvent such as acetone, methyl ethyl ketone, or an aprotic polar solvent such as N,N-dimethylformamide may, for example, be mentioned.

Process <4>

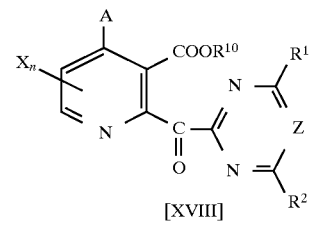

[XVI]

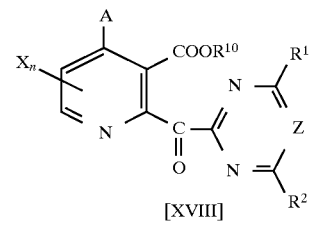

[XVIII]

(wherein $R^{10}$ is an optionally substituted alkyl group, an optionally substituted benzyl group, an alkenyl group or an alkynyl group, and A, X, n, $R^1$, $R^2$, Z and $L^1$ are as defined above.)

A compound represented by the general formula [XVIII] can be prepared by reacting a compound represented by the general formula [XVI] with a compound represented by the general formula [XVII] in a suitable solvent in the presence of at least the equivalent amount of a base at a temperature within a range of from 0° C. to the boiling point of the solvent for from 0.5 to 24 hours.

The base and the solvent to be used may be the same as those described for the production of [XII] in Process <1>.

Process <5>

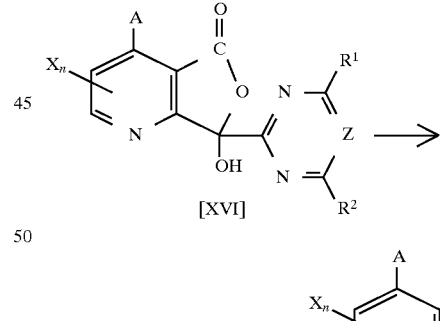

[XVI]

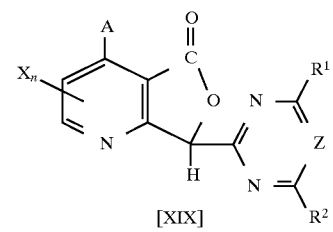

[XIX]

(wherein A, X, n, $R^1$, $R^2$ and Z are as defined above.)

A compound represented by the general formula [XIX] can be prepared by reducing a compound represented by the general formula [XVI] with a reductant such as sodium boron hydride in an alcoholic solvent such as ethanol at a temperature within a range of from 0° C. to room temperature.

Process <6>

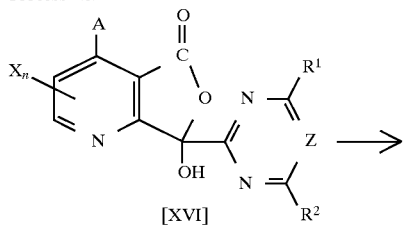

[XVI]

[XX]

(wherein M is the equivalent amount of a cation of an alkali metal, an alkaline earth metal, ammonium or an organic ammonium ion, and A, X, n, $R^1$, $R^2$ and Z are as defined above.)

A compound represented by the general formula [XX] can be prepared by reacting a compound represented by the general formula [XVI] with the equivalent amount of a base in a suitable solvent at a temperature within a range from room temperature to the boiling point of the solvent for from 0.5 to 24 hours.

As the base, an alkali metal hydride such as sodium hydride or potassium hydride, an alkali metal alkoxide such as sodium methoxide or sodium ethoxide, an alkali metal or alkaline earth metal hydroxide such as sodium hydroxide or calcium hydroxide, an alkali metal or alkaline earth metal carbonate such as sodium carbonate or calcium carbonate, ammonia, or an organic amine such as isopropylamine, may, for example, be used.

As the solvent, a hydrocarbon solvent such as toluene or xylene, an alcoholic solvent such as methanol or ethanol, an ethereal solvent such as diethyl ether or tetrahydrofuran, a non-polar protic solvent such as N,N-dimethylformamide or other solvent such as acetonitrile or water, may be used.

Process <7>

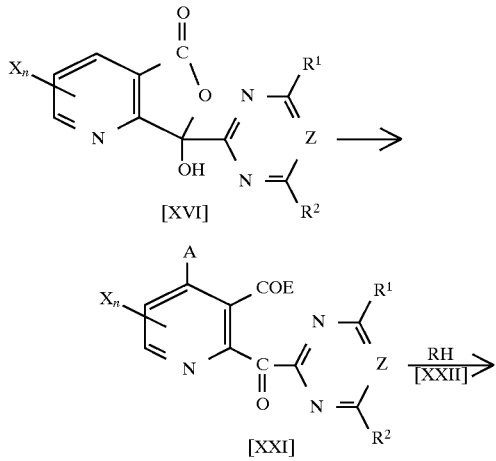

[XVI]

[XXI]

-continued

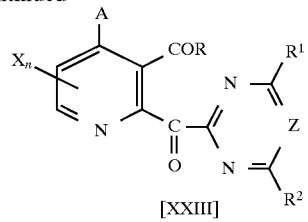

[XXIII]

(wherein E is a halogen atom, a 1-imidazolyl group or a substituted amidinoxy group, and A, X, n, $R^1$, $R^2$, R and Z are as defined above.)

A compound represented by the general formula [XXIII] can be prepared by reacting a compound represented by the general formula [XVI] with at least the equivalent amount of a condensation agent in a suitable solvent at a temperature within a range of from −10° C. to the boiling point of the solvent for from 0.5 to 24 hours to give an intermediate compound represented by the general formula [XXI], and then after isolation or without isolation, reacting the intermediate compound with a compound represented by the general formula [XXII] in the presence of at least the equivalent amount of a base in a suitable solvent at a temperature within a range of from −10° C. to the boiling point of the solvent for from 0.5 to 24 hours.

As the condensation agent, thionyl chloride, oxalyl dichloride, chlorocarbonic ester, carbonyldiimidazole or carbodiimide may be used.

With respect to the base and the solvent to be used, as the base, an alkali metal such as metal lithium, metal sodium or metal potassium, an organic lithium reagent such as n-butyl lithium or lithium diisopropylamide (LDA), an alkali metal hydride such as sodium hydride or potassium hydride, an alkali metal alkoxide such as potassium t-butoxide, an alkali metal carbonate such as sodium carbonate or potassium carbonate, an alkali metal hydroxide such as sodium hydroxide or potassium hydroxide, or an organic amine such as triethylamine or N,N-dimethylaminopyridine may be used.

As the solvent, a hydrocarbon solvent such as toluene or xylene, a halogenated hydrocarbon solvent such as dichloromethane or chloroform, an ethereal solvent such as diethyl ether, tetrahydrofuran or 1,4-dioxane, an ester solvent such as ethyl acetate, a ketone solvent such as acetone, an aprotic polar solvent such as N,N-dimethylformamide or dimethyl sulfoxide, or other solvent such as acetonitrile may be used.

Process <8>

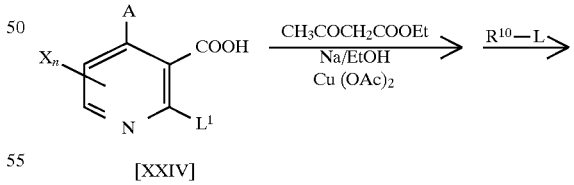

[XXIV]

[XXV]

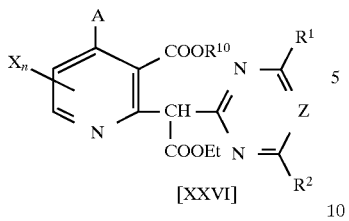

[XXVI]

(wherein A, $R^1$, $R^2$, $R^{10}$, L, $L^1$, X, Z and n are as defined above.)

A compound represented by the general formula [XXVI] can be prepared by reacting a compound represented by the general formula [XXV] with a compound represented by the general formula [XXVII] in a polar solvent such as N,N-dimethylformamide in the presence of a base of potassium t-butoxide at a temperature within a range of from 0° C. to the boiling point of the solvent for from 0.5 to 24 hours.

A compound represented by the general formula [XXV] can be prepared by reacting a compound represented by the general formula [XXIV] with ethyl acetoacetate in the presence of copper acetate and sodium ethoxide in an alcohol for esterification.

Process <9>

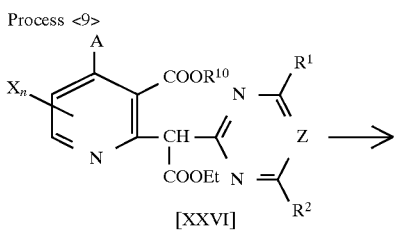

[XXVI]

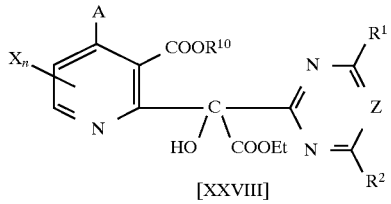

[XXVIII]

(wherein A, X, $R^{10}$, $R^1$, $R^2$, Z and n are as defined above.)

A compound represented by the general formula [XXVIII] can be prepared by reacting a compound represented by the general formula [XXVI] with an organic peroxide such as m-chloroperbenzoic acid in a halogenated hydrocarbon solvent such as dichloromethane or chloroform at room temperature for from 0.5 to 24 hours.

Process <10>

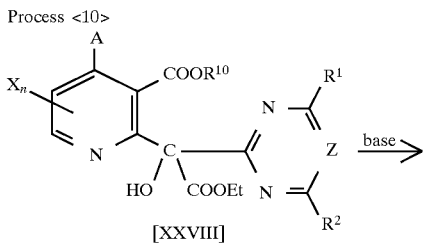

[XXVIII]

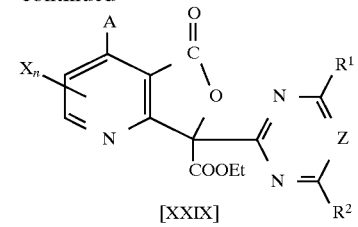

[XXIX]

(wherein A, X, $R^{10}$, $R^1$, $R^2$, Z and n are as defined above.)

A compound represented by the general formula [XXIX] can be prepared by reacting a compound represented by the general formula [XXVIII] in the presence of a base in a suitable solvent at a temperature within a range of from 0° C. to the boiling point of the solvent for from 0.5 to 24 hours.

As the base to be used, an alkali metal such as metal lithium, metal sodium or metal potassium, an alkali metal hydride such as sodium hydride or potassium hydride, an alkali metal alkoxide such as potassium t-butoxide, an alkali metal carbonate such as sodium carbonate or potassium carbonate, or an alkali metal hydroxide such as sodium hydroxide or potassium hydroxide may be used.

As the solvent, a hydrocarbon solvent such as toluene or xylene, a halogenated hydrocarbon solvent such as dichloromethane or chloroform, an ethereal solvent such as diethyl ether, tetrahydrofuran or 1,4-dioxane, an ester solvent such as ethyl acetate, a ketone solvent such as acetone, an aprotic polar solvent such as N,N-dimethylformamide or dimethyl sulfoxide, or other solvent such as acetonitrile may be used.

Examples of synthesis of novel intermediate compounds of the general formulae [VIII] and [IX] are given in the following Reference Examples.

REFERENCE EXAMPLE 1

Synthesis of methyl 2-cyano-5-N,N-dimethylamino-3-(2-thienyl)-2,4-pentadienoate (Intermediate No. 275)

400 g of 2-acetylthiophene, 314 g of methyl cyanoacetate and 48.8 g of ammonium acetate were dissolved in a mixture of 153 ml of acetic acid and 1.5 l of toluene, and the resulting reaction solution was refluxed under heating for 8 hours while water was removed. The reaction solution was washed sufficiently with water and then dried over anhydrous magnesium sulfate. Removal of the solvent by distillation was followed by vacuum distillation (b.p. 110°–140° C./0.05 mmHg) to give 263.4 g of methyl 2-cyano-3-(2-thienyl) crotonate. (Yield 40%)

Then, 38.9 g of methyl 2-cyano-3-(2-thienyl)crotonate and 33.4 g of N,N-dimethylformamide dimethyl acetal were dissolved in 600 ml of methanol, and the resulting solution was refluxed under heating for 30 minutes. The solvent was concentrated, and the resulting oily substance was crystallized from methanol to obtained 40 g of the desired compound. (Yield 44%) m.p.: 140°–143° C.

REFERENCE EXAMPLE 2

Synthesis of methyl 2-bromo-4-(5-chloro-2-thienyl) nicotinate (Intermediate No. 283)

44.6 g of methyl 2-cyano-5-N,N-dimethylamino-3-(5-chloro-2-thienyl)-2,4-pentadienoate was dissolved in 300 ml of acetic acid, and 146 g of 25% solution of hydrogen bromide in acetic acid was added dropwise thereto under cooling with ice. Then, this reaction solution was stirred at room temperature for 6 hours, then poured into water and extracted with ethyl acetate. The extract was sufficiently washed with water and dried over anhydrous magnesium sulfate, and the solvent was distilled off to obtain 35 g of the desired compound. (Yield 78.3%) Refractive index: 1.6408

Specific examples of intermediates obtained likewise are listed in the following Tables 4 and 5.

TABLE 4

| Intermediate No. | A | $R^7$ | $R^9$ | Melting point (°C.) or refractive index ($n_D^{20}$) |
|---|---|---|---|---|
| 275 | thiophen-2-yl (S) | H | H | 140~143 |
| 276 | thiophen-3-yl (S) | H | H | 180~183 |
| 277 | thiophen-2-yl (S) | H | $CH_3$ | 99~102 |
| 278 | pyridin-4-yl (N) | H | H | 206~208 |
| 279 | phenyl | H | H | 144~146 |
| 280 | 4-F-phenyl | H | H | 198.5~200.5 |
| 281 | 4-$CH_3O$-phenyl | H | H | 175~178 |

TABLE 5

| Intermediate No. | A | $R^7$ | $R^8$ | $R^9$ | L | Melting point (°C.) or refractive index ($n_D^{20}$) |
|---|---|---|---|---|---|---|
| 282 | thiophen-2-yl (S) | H | $CH_3$ | H | Br | 59~61 |
| 283 | 5-Cl-thiophen-2-yl (S) | H | $CH_3$ | H | Br | 1.6408 |
| 284 | 5-$CH_3$-thiophen-2-yl (S) | H | $CH_3$ | H | Br | 1.6230 |
| 285 | 5-$CH_3$-furan-2-yl (O) | H | $CH_3$ | H | Br | 58~60 |
| 286 | pyridin-4-yl (N) | H | $CH_3$ | H | Br | 133~135.5 |
| 287 | pyridin-3-yl (N) | H | $CH_3$ | H | Br | 100~105 |
| 288 | furan-2-yl (O) | H | $CH_3$ | H | Br | 97~98 |
| 289 | 4-Cl-phenyl | H | $CH_3$ | H | Br | 73~76 |
| 290 | 4-$CH_3O$-phenyl | H | $CH_3$ | H | Br | 89~90.5 |
| 291 | 4-F-phenyl | H | $CH_3$ | H | Br | 79~82 |
| 292 | 5-$CH_3O$-thiophen-2-yl (S) | H | $CH_3$ | H | Br | 61~63 |

BEST MODE FOR CARRYING OUT THE INVENTION

Now, the processes for the production of compounds of the present invention will be concretely described with reference to Examples.

EXAMPLE 1

Preparation of methyl 2-[α-cyano-(4,6-dimethoxypyrimidin-2-yl)methyl]-4-(3-pyridyl) nicotinate (Compound No. 49)

1.9 g of 60% sodium hydride was weighed out, and 100 ml of N,N-dimethylformamide was added to it. The resulting mixture was stirred under cooling with ice. Then, 4.49 g of 4,6-dimethoxypyrimidin-2-ylacetonitrile was added thereto, and the reaction solution was stirred at room temperature for 30 minutes. This reaction mixed solution was cooled again with ice, and 7.0 g of methyl 2-bromo-4-(3-pyridyl)nicotinate was added thereto. The reaction mixed solution was stirred at 80° C. for 3 hours and then poured into water and acidified with 20% hydrochloric acid. The precipitated crystals were filtered off, washed with isopropyl ether and dried in vacuo to obtain 4.8 g (yield 57.8%) of the desired compound as orange crystals. m.p.: >300° C.

EXAMPLE 2

Preparation of 7-cyano-7-(4,6-dimethoxypyrimidin-2-yl)-4-(2-thienyl)furo[3,4-b]pyridin-5(7H)one (Compound No. 208)

1.01 g of methyl 2-[α-cyano-(4,6-dimethoxypyrimidin-2-yl)methyl]-4-(2-thienyl)nicotinate was weighed out, and 50 ml of chloroform was added thereto. Then, the mixture was stirred at −10° C. 0.75 g of 70% m-chloroperbenzoic acid was added thereto, and the mixture was stirred at room temperature for 30 minutes. The mixture was washed with saturated sodium thiosulfate and water and dried over anhydrous magnesium sulfate. The solvent was distilled off, and the resulting residue was purified by silica gel column chromatography (developing solvent: ethyl acetate/hexane=½) to obtain 0.40 g of the desired compound (yield 41.0%) as yellow crystals. m.p.: 187°–188.5° C.

EXAMPLE 3

Preparation of 7-(4,6-dimethoxypyrimidin-2-yl)-4-(2-furyl)-7-hydroxyfuro[3,4-b]pyridin-5(7H)one (Compound No. 229)

0.42 g of 7-cyano-7-(4,6-dimethoxypyrimidin-2-yl)-4-(2-furyl)furo[3,4-b]pyridin-5(7H)one was weighed out, and 14 ml of tetrahydrofuran was added thereto. The mixture was stirred under cooling with ice. 14 ml of 0.25N sodium hydroxide aqueous solution was added thereto dropwise, and the mixture was stirred at room temperature for 30 minutes. The mixture was poured into water, and the aqueous layer was washed with ethyl acetate twice, acidified with 10% hydrochloric acid and extracted with 100 ml of ethyl acetate. The extract was washed with saturated aqueous sodium chloride solution and then dried over anhydrous magnesium sulfate. The solvent was distilled off, and the resulting crystals were washed with methyl alcohol to obtain 0.40 g (yield 94.6%) of the desired compound as yellow crystals. m.p.: 198°–204° C.

EXAMPLE 4

Preparation of methyl 2-(4,6-dimethoxypyrimidin-2-ylcarbonyl)-4-(2-furyl)nicotinate (Compound No. 38)

2.1 g of 7-(4,6-dimethoxypyrimidin-2-yl)-4-(2-furyl)-7-hydroxyfuro[3,4-b]pyridin-5(7H)one was weighed out, and 50 ml of N,N-dimethylformamide and 0.82 g of potassium carbonate were added thereto. The mixture was stirred at room temperature. 0.8 g of methyl iodide was added thereto dropwise, and the mixture was stirred at room temperature overnight, then poured into water and extracted 200 ml of ethyl acetate. The extract was washed with saturated aqueous sodium chloride solution and dried over anhydrous magnesium sulfate. The solvent was distilled off, and the residue was purified by silica gel column chromatography (developing solvent: ethyl acetate/hexane=⅓) to obtain 1.1 g (yield 50.7%) of the desired compound as brown crystals. m.p.: 135°–140° C.

EXAMPLE 5

Preparation of 7-(4,6-dimethoxypyrimidin-2-yl)-4-(2-thienyl)furo[3,4-b]pyridin-5(7H)one (Compound No. 210)

0.7 g of 7-(4,6-dimethoxypyrimidin-2-yl)-7-hydroxy-4-(2-thienyl)furo[3,4-b]pyridin-5(7H)one was dissolved in 30 ml of ethyl alcohol, and while this solution was stirred under cooling with ice, 0.07 g of sodium boron hydride was added thereto. The mixture was stirred at room temperature for 30 minutes, and then the ethyl alcohol was removed by distillation in vacuo. The residue was acidified with 10% hydrochloric acid and extracted with 200 ml of ethyl acetate. The extract was washed with saturated aqueous sodium chloride solution and dried over anhydrous magnesium sulfate. The solvent was distilled off, and the resulting residue was purified by silica gel column chromatography (developing solvent: ethyl acetate/hexane=½) to obtain 0.35 g (yield 52.0%) of the desired compound. m.p.: 120°–123° C.

EXAMPLE 6

Preparation of sodium 2-(4,6-dimethoxypyrimidin-2-ylcarbonyl)-4-(2-thienyl)nicotinate (Compound No. 96)

0.4 g of 7-(4,6-dimethoxypyrimidin-2-yl)-4-(2-thienyl)-7-hydroxyfuro[3,4-b]pyridin-5(7H)one was dissolved in 100 ml of benzene, and 0.05 g of 60% sodium hydride was added thereto under cooling with ice. Then the resulting mixture was stirred at room temperature for one day, and the precipitated crystals were sufficiently washed with benzene to obtain 0.4 g (yield 97%) of the desired compound. m.p.: >300° C.

EXAMPLE 7

Preparation of methyl 2-[α-cyano-(4,6-dimethoxypyrimidin-2-yl)methyl]-4-phenylnicotinate (Compound No. 60)

3.2 g of 60% sodium hydride was washed with n-hexane, and 100 ml of N,N-dimethylformamide was added thereto. 6 g of 4,6-dimethoxypyrimidin-2-ylacetonitrile was added gradually thereto under cooling with ice, and the mixture was stirred for 30 minutes. Then, 10 g of methyl 2-bromo-4-phenylnicotinate was added, and the reaction solution was stirred at 80° C. for 2 hours. The reaction solution was poured into ice water and adjusted to pH 2–3 with dilute hydrochloric acid. The precipitated crystals were collected by filtration and washed sufficiently with toluene and ethyl acetate. The crystals thus obtained were dried to obtain 5 g (yield 38%) of the desired compound. m.p.: 198°–199° C.

EXAMPLE 8

Preparation of methyl 2-[α-cyano-a-hydroxy-1-(4,6-dimethoxypyrimidin-2-yl)methyl]-4-phenylnicotinate (Compound No. 95)

3.9 g of methyl 2-[α-cyano-(4,6-dimethoxypyrimidin-2-yl)methyl]-4-phenylnicotinate was suspended in 50 ml of chloroform, and 3 g of 70% m-chloroperbenzoic acid was added thereto. The suspension was stirred at room temperature for 30 minutes, then washed sufficiently with aqueous sodium sulfite solution, saturated aqueous sodium hydrogencarbonate solution and saturated aqueous sodium chloride solution, and dried over anhydrous magnesium sulfate. The solvent was distilled off, and the residue was crystallized from a solvent mixture of isopropyl ether and ethyl acetate to obtain 2.9 g (yield 73%) of the desired compound. m.p.: 126°–129° C.

EXAMPLE 9

Preparation of 7-cyano-7-(4,6-dimethoxypyrimidin-2-yl)-4-phenylfuro[3,4-b]pyridin-5(7H)one (Compound No. 244)

1 g of methyl 2-[α-cyano-(4,6-dimethoxypyrimidin-2-yl)methyl]-4-phenylnicotinate was suspended in 20 ml g of dichloromethane, and 0.8 g of 70% m-chloroperbenzoic acid was added thereto. The reaction suspension was stirred at room temperature for 2 hours, then washed sufficiently with aqueous sodium hydrogensulfite solution, saturated aqueous sodium hydrogencarbonate solution and saturated aqueous sodium chloride solution and dried. Then, the solvent was distilled off. The resulting crude product was dissolved in 20 ml of ethanol, and 0.5 ml of concentrated hydrochloric acid was added thereto. The mixture was stirred at 40° C. for 30 minutes. The ethanol was distilled off, and ice water was added to the residue. The precipitated crystals were recrystallized from ethanol to obtain 0.31 g (yield 31%) of the desired compound. m.p.: 196°–198° C.

EXAMPLE 10

Preparation of 7-(4,6-dimethoxypyrimidin-2-yl)-7-hydroxy-4-(4-chlorophenyl)furo[3,4-b]pyridin-5(7H)one (Compound No. 248)

2.2 g of methyl 2-[α-cyano-(4,6-dimethoxypyrimidin-2-yl)methyl]-4-(4-chlorophenyl)nicotinate was dissolved in 50 ml g of chloroform, and 1.07 g of 70% m-chloroperbenzoic acid was added thereto. The resulting reaction solution was stirred at room temperature for 1 hour, then washed well with saturated aqueous sodium hydrogensulfite solution, saturated sodium hydrogencarbonate and saturated aqueous sodium chloride solution and dried over anhydrous sodium sulfate. The solvent was distilled off, and the resulting crude product was dissolved in 30 ml of tetrahydrofuran. 30 ml of an aqueous solution of 0.7 g of sodium hydroxide was added thereto, and the resulting reaction solution was stirred at room temperature for 2 hours. The reaction solution was poured into ice water, adjusted to pH 2–3 with dilute hydrochloric acid and extracted with ethyl acetate. The extract was sufficiently washed with water and then dried over anhydrous magnesium sulfate. The solvent was distilled off, and the resulting crude crystals were sufficiently washed with ethanol to obtain 1.5 g (yield 75%) of the desired compound. m.p.: 228°–231° C.

EXAMPLE 11

Preparation of 7-(4,6-dimethoxypyrimidin-2-yl)-4-phenylfuro[3,4-b]pyridin-5(7H)one (Compound No. 246)

1 g of 7-(4,6-dimethoxypyrimidin-2-yl)-7-hydroxy-4-phenylfuro[3,4-b]pyridin-5(7H)one was dissolved in 30 ml of ethanol, and 0.1 g of sodium boron hydride was added thereto at room temperature. The mixture was stirred at room temperature for 6 hours, and the ethanol was distilled off. Ice water was added to the residue, and the mixture was adjusted to pH 2–3 with dilute hydrochloric acid and then extracted with ethyl acetate. The extract was sufficiently washed with water and dried over anhydrous magnesium sulfate, and then the solvent was distilled off. The resulting crude product was purified by silica gel column chromatography to obtain 0.7 g (yield 73%) of the desired compound. m.p.: 151°–153.5° C.

EXAMPLE 12

Preparation of benzyl 2-(4,6-dimethoxypyrimidin-2-ylcarbonyl)-4-phenylnicotinate (Compound No. 62)

0.5 g of 7-(4,6-dimethoxypyrimidin-2-yl)-7-hydroxy-4-phenylfuro[3,4-b]pyridin-5(7H)one was dissolved in 10 ml of N,N-dimethylformamide, and 0.2 g of potassium carbonate was added thereto. Then, the reaction solution was stirred sufficiently. 0.23 g of benzyl bromide was added dropwise to the reaction solution at room temperature, and the reaction solution was stirred for one day. The reaction solution was poured into ice water and extracted with ethyl acetate. The extract was sufficiently washed with water and then dried over anhydrous magnesium sulfate. The solvent was distilled off, and the resulting crude crystals were washed with isopropyl ether to obtain 0.5 g (yield 80%) of the desired compound. m.p.: 124°–126° C.

EXAMPLE 13

Preparation of sodium 2-(4,6-dimethoxypyrimidin-2-ylcarbonyl)-4-(4-chlorophenyl)nicotinate (Compound No. 97)

0.4 g of 7-(4,6-dimethoxypyrimidin-2-yl)-4-(4-chlorophenyl)-7-hydroxyfuro[3,4-b]pyridin-5-(7H)one was dissolved in 100 m of toluene, and 0.05 g of 60% sodium hydride was added thereto. The mixture was stirred at room temperature for one day. The precipitated crystals were collected by filtration and sufficiently washed with acetone to obtain 0.25 g (yield 60%) of the desired compound. m.p.: 263°–267° C.

EXAMPLE 14

Preparation of 2-(4,6-dimethoxypyridin-2-ylcarbonyl)-3-(imidazol-1-ylcarbonyl)-4-phenylpyridine (Compound No. 112)

1.5 g of 7-(4,6-dimethoxypyridin-2-yl)-7-hydroxy-4-phenylfuro[3,4-b]pyridin-5(7H)one was dissolved in 20 ml of tetrahydrofuran, and 0.6 g of N,N-carbonyldiimidazole was added thereto. After stirred at room temperature for 2 days, the reaction solution was poured into water and extracted with ethyl acetate. The extract was sufficiently washed with water and dried over anhydrous magnesium sulfate. The solvent was distilled off, and the resulting residue was crystallized from isopropyl ether to obtain 1.3 g (yield 76.5%) of the desired compound. m.p.: 126°–128° C.

EXAMPLE 15

Preparation of ethyl 4-(5-chlorothiophen-2-yl)-2-[(4,6-dimethoxypyridin-2-yl)-α-ethoxycarbonylmethyl]-nicotinate (Compound No. 103)

2.9 g of sodium was dissolved in 80 ml of ethanol, and 9.7 g of acetoacetic ester was added thereto at room temperature. The mixture was stirred for 15 minutes. A mixture of 0.4 g of copper acetate and 14 g of 2-bromo-4-(5-chlorothiopen-2-yl)nicotinic acid was added thereto, and the resulting reaction solution was refluxed for 3 hours. After completion of the reaction, 40 ml of acetic acid was added thereto, and the solvent was distilled off. The residue was extracted with ethyl acetate, and the extract was washed with water and dried over anhydrous magnesium sulfate. The ethyl acetate was distilled off, and the residue was dissolved in 50 ml of N,N-dimethylformamide. Then, 9.8 g of ethyl iodide and 10 g of potassium carbonate were added to the solution. The solution was allowed to react at room temperature for 3 hours. After completion of the reaction, the reaction solution was poured into water and extracted with ethyl acetate. The extract was washed with water and then dried over anhydrous magnesium sulfate. The ethyl acetate was distilled of, and the residue was purified by silica gel column chromatography (hexane:ethyl acetate=5:1) to obtain 8.9 g of ethyl 4-(5-chlorothiophen-2-yl)- 2-(α-ethoxycarbonylmethyl)nicotinate in a 50% yield.

Next, 2.9 g of potassium t-butoxide was added to 50 ml of N,N-dimethylformamide. To the resulting mixture, 8.9 g of ethyl 4-(5-chlorothiophen-2-yl)-2-(α-ethoxycarbonylmethyl)nicotinate dissolved in N,N-dimethylformamide was added dropwise at −10° C., and the resulting reaction solution was stirred at room temperature for 1 hour. 5.6 g of 4,6-dimethoxy-2-methylsulfonylpyrimidine was added thereto, and the reaction solution was stirred at a temperature of from 60° C. to 80° C. for 8 hours. After completion of the reaction, the reaction solution was poured into water and brought to pH 4–5 and extracted with ethyl acetate. The extract was washed with water and dried over anhydrous magnesium sulfate. The ethyl acetate was distilled off, and the residue was purified by silica gel column chromatography (hexane:ethyl acetate=5:1) to obtain 2.7 g (yield 23%) of the desired compound. m.p.: 127°–132° C.

EXAMPLE 16 s-ethyl 2-(4,6-dimethoxypyrimidin-2-ylcarbonyl)-4-(4-chlorophenyl)pyridine-3-carbothioate (Compound No. 152)

0.5 g of 7-(4,6-dimethoxypyrimidin-2-yl)-7-hydroxy-4-(4-chlorophenyl)furo[3,4-b]pyridin-5(7H)one was dissolved in 20 ml of dichloromethane, and then 0.29 g of 3-(3-dimethylaminopropyl)-1-ethyl-carbodiimide hydrochloride and 0.09 g of N,N-dimethylaminopyridine were added to the solution. The mixture was stirred at room temperature for 30 minutes. Then, 0.08 g of ethyl mercaptan was added thereto, and the reaction solution was stirred at room temperature for 2 hours. The reaction solution was sufficiently washed with water and dried over anhydrous magnesium sulfate. The solvent was distilled off, and the resulting residue was crystallized from diisopropyl ether to obtain 0.45 (yield 81%) of the desired compound. m.p.: 205°–207° C.

EXAMPLE 17

Preparation of ethyl 4-(5-chlorothiophen-2-yl)-2-[(4,6-dimethoxypyrimidin-2-yl)-α-ethoxycarbonyl-α-hydroxymethyl]nicotinate (Compound No. 102)

1.0 g of ethyl 4-(5-chlorothiophene-2-yl)-2-[(4,6-dimethoxypyrimidin-2-yl)-α-ethoxycarbonylmethyl] nicotinate was dissolved in 10 ml of chloroform, and 0.6 g of 80% m-chloroperbenzoic acid was added thereto. After stirred at room temperature for 2 hours, the reaction solution was washed with saturated aqueous sodium hydrogencarbonate solution and saturated aqueous sodium chloride solution and then dried over anhydrous magnesium sulfate. The solvent was distilled off, and the resulting residue was crystallized from diisopropyl ether to obtain 0.9 (yield 97%) of the desired compound. m.p.: 109°–112° C.

EXAMPLE 18

Preparation of 4-(5-chlorothiophen-2-yl)-7-(4,6-dimethoxypyrimidin-2-yl)-7-ethoxycarbonyl-furo[3,4,b]pyridin-5-(7H)one (Compound No. 272)

0.9 g of ethyl 4-(5-chlorothiophen-2-yl)-2[4,6-dimethoxypyrimidin-2-yl)-α-ethoxycarbonyl-α-hydroxymethyl]nicotinate was dissolved in 10 ml of tetrahydrofuran, and 0.08 g of 60% sodium hydride was added thereto under cooling with ice. After stirred at room temperature for 1 hour, the reaction solution was poured into ice water and extracted with ethyl acetate. The extract was sufficiently washed with saturated aqueous sodium chloride solution and then dried over anhydrous magnesium sulfate. The solvent was distilled off, and the resulting residue was crystallized from diisopropyl ether to obtain 0.4 g (yield 79%) of the desired compound. m.p.: 150°–156° C.

The herbicide of the present invention comprises a nicotinic acid derivative of the general formula [I] or [II] as an active ingredient.

For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier, a surfactant, a dispersant or an adjuvant which is commonly used for formulations.

The carrier to be used for such formulations, may, for example, be a solid carrier such as zeeklite, talc, bentonite, clay, kaolin, diatomaceous earth, white carbon, vermiculite, calcium carbonate, slaked lime, siliceous sand, ammonium sulfate or urea, or a liquid carrier such as isopropyl alcohol, xylene, cyclohexanone or methylnaphthalene.

As the surfactant and dispersant, a metal salt of alkylbenzenesulfonic acid, a metal salt of dinaphthylmethanedisulfonic acid, a salt of an alcohol sulfuric acid ester, an alkylaryl sulfonate, a lignin sulfonate, a polyoxyethylene glycol ether, a polyoxyethylene alkyl aryl ether or a polyoxyethylene sorbitol monoalkylate may, for example, be mentioned. The adjuvant may, for example, be carboxymethyl cellulose, polyethylene glycol or gum arabic. In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in the case of a dust or a granule, the proportion of the active ingredient is selected suitably within a range of from 0.01 to 10% by weight, preferably from 0.05 to 5% by weight. In the case of an emulsifiable concentrate or a wettable powder, the proportion is selected suitably within a range of from 1 to 50% by weight, preferably from 5 to 30% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In the case of an emulsifiable concentrate or a wettable powder which is used in a liquid state, the dose of the active ingredient is selected suitably within a range of from 0.1 to 50,000 ppm, preferably from 10 to 10,000 ppm.

Further, the compound of the present invention may be used in combination with an insecticide, a fungicide, another herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1

Wettable powder

To 10 parts of Compound No. 244, 0.5 part of polyoxyethylene octyl phenyl ether, 0.5 part of sodium salt of β-naphthalenesulfonic acid-formalin condensate, 20 parts of diatomaceous earth and 69 parts of clay were mixed, and the mixture was pulverized to obtain a wettable powder.

FORMULATION EXAMPLE 2

Wettable powder

To 10 parts of Compound No. 105, 0.5 part of polyoxyethylene octyl phenyl ether, 0.5 part of sodium salt of β-naphthalenesulfonic acid-formalin condensate, 20 parts of diatomaceous earth, 5 parts of white carbon and 64 parts of clay were mixed, and the mixture was pulverized to obtain a wettable powder.

FORMULATION EXAMPLE 3

Wettable powder

To 10 parts of Compound No. 3, 0.5 part of polyoxyethylene octyl phenyl ether, 0.5 part of sodium salt of β-naphthalenesulfonic acid-formalin condensate, 20 parts of diatomaceous earth, 5 parts of white carbon and 64 parts of calcium carbonate were mixed, and the mixture was pulverized to obtain a wettable powder.

FORMULATION EXAMPLE 4

Emulsifiable concentrate

To 30 parts of Compound No. 245, 60 parts of a mixture comprising equal amounts of xylene and isophorone and 10 parts of a surfactant mixture comprising a polyoxyethylene sorbitol alkylate, a polyoxyethylene alkyl aryl polymer and an alkylaryl sulfonate, were added, and the mixture was thoroughly stirred to obtain an emulsifiable concentrate.

FORMULATION EXAMPLE 5

Granule 10 parts of Compound No. 246, 80 parts of a bulking agent comprising a 1:3 mixture of talc and bentonite, 5 parts of white carbon, 5 parts of a surfactant mixture comprising a polyoxyethylene sorbitol alkylate, a polyoxyethylene alkyl aryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

The compounds of the present invention exert excellent herbicidal effects against various weeds which cause trouble in upland fields, for example, broad leaved weeds such as birdseye speedwell, Hungarian chamomile, shepherd's purse, pale smartweed, slender amaranth, common lambsquater, velvetleaf, prickly sida, hempsesbania, blue morningglory and common cocklebur, perennial and annual cyperaceous weeds such as purple nutsedge, yellow nutsedge, cyperus brevifolius, rice flatsedge, and gramineous weeds such as barnyardgrass, green foxtail, annual bluegrass, Johnsongrass, blackgrass and wild oat, over a broad period from the pre-emergence season to the growing season. The compounds of the present invention can control annual paddy weeds such as barnyardgrass, smallflower umbrellaplant and monochoria and perennial paddy weeds such as Japanese ribbon wapato, arrowhead, flat sedge, water chestnut, bulrush and narrowleaf waterplantain.

Further, the compounds of the present invention are highly safe especially to crop plants such as wheat and barley.

Now, the herbicidal effects of the compounds of the present invention will be described with reference to Test Examples.

TEST EXAMPLE 1

(Test on herbicidal effects by paddy field soil treatment)

Plastic pots of 100 cm$^2$ were filled with paddy field soil. After puddling and leveling, seeds of barnyardgrass (Ec), monochoria (Mo) and bulrush (Sc) were sown in the pots and the pots were flooded to a water depth of 3 cm. Next day, wettable powders prepared in accordance with Formulation Example 1 were diluted with water and applied dropwise to the water surfaces. The dose was 100 g of the active ingredient per 10 ares. The plants were then cultured in a green house, and the evaluation of the herbicidal effects was conducted on the 21st day after the application in accordance with the standards as identified in Table 6. The results are shown in Table 7.

TABLE 6

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10 and less than 30% |
| 0 | Herbicidal effect or phytotoxicity: 0 to less than 10% |

TABLE 7

| Compound No. | Herbicidal effects | | |
|---|---|---|---|
| | Ec | Mo | Sc |
| 1 | 5 | 5 | 5 |
| 2 | 4 | 5 | 4 |
| 23 | 5 | 5 | 5 |
| 37 | 5 | 5 | 5 |
| 38 | 5 | 5 | 5 |
| 60 | 5 | 5 | 5 |
| 61 | 5 | 5 | 5 |
| 62 | 5 | 5 | 5 |
| 77 | 5 | 5 | 5 |
| 95 | 5 | 5 | 5 |
| 98 | 4 | 5 | 5 |
| 99 | 5 | 5 | 5 |
| 100 | 4 | 5 | 5 |
| 102 | 5 | 5 | 5 |
| 103 | 5 | 5 | 5 |
| 104 | 5 | 5 | 5 |
| 105 | 5 | 4 | 5 |
| 106 | 5 | 5 | 5 |
| 107 | 5 | 5 | 5 |
| 108 | 5 | 5 | 5 |
| 112 | 4 | 5 | 5 |
| 135 | 5 | 5 | 5 |
| 136 | 5 | 5 | 5 |
| 137 | 5 | 5 | 5 |
| 138 | 4 | 5 | 5 |
| 144 | 5 | 5 | 5 |
| 145 | 5 | 5 | 5 |
| 146 | 5 | 5 | 5 |
| 147 | 5 | 5 | 5 |
| 148 | 5 | 5 | 5 |
| 149 | 5 | 5 | 5 |
| 150 | 5 | 5 | 5 |
| 152 | 5 | 5 | 5 |
| 156 | 4 | 5 | 5 |
| 160 | 5 | 5 | 5 |
| 161 | 5 | 5 | 5 |
| 162 | 5 | 5 | 5 |
| 228 | 5 | 5 | 5 |
| 229 | 5 | 5 | 5 |
| 244 | 5 | 5 | 5 |
| 245 | 5 | 5 | 5 |
| 246 | 5 | 5 | 5 |
| 272 | 5 | 5 | 5 |
| 273 | 5 | 5 | 5 |

TABLE 8

| Compound No. | Herbicidal effects | | | | |
|---|---|---|---|---|---|
| | Ec | Po | Am | Ch | Ci |
| 1 | 5 | 5 | 5 | 5 | 5 |
| 2 | 4 | 5 | 5 | 5 | 5 |
| 37 | 5 | 5 | 5 | 5 | 5 |
| 38 | 5 | 5 | 5 | 5 | 5 |
| 60 | 5 | 5 | 5 | 5 | 5 |
| 61 | 5 | 5 | 5 | 5 | 5 |
| 62 | 5 | 5 | 5 | 5 | 5 |
| 77 | 5 | 5 | 5 | 5 | 5 |
| 95 | 5 | 5 | 5 | 5 | 5 |
| 98 | 5 | 5 | 5 | 5 | 5 |
| 99 | 5 | 5 | 5 | 5 | 5 |
| 100 | 5 | 5 | 5 | 5 | 5 |
| 101 | 3 | 5 | 5 | 5 | 5 |
| 102 | 5 | 5 | 5 | 5 | 5 |
| 103 | 3 | 5 | 5 | 5 | 5 |
| 104 | 3 | 5 | 5 | 4 | 5 |
| 105 | 5 | 5 | 5 | 5 | 5 |
| 106 | 5 | 5 | 5 | 5 | 5 |
| 107 | 5 | 5 | 5 | 5 | 5 |
| 108 | 5 | 5 | 5 | 5 | 5 |
| 112 | 5 | 5 | 5 | 5 | 5 |
| 135 | 5 | 5 | 5 | 5 | 5 |
| 136 | 5 | 5 | 5 | 5 | 5 |
| 137 | 5 | 5 | 5 | 5 | 5 |
| 138 | 5 | 5 | 5 | 5 | 5 |
| 144 | 5 | 5 | 5 | 5 | 5 |
| 145 | 4 | 5 | 5 | 5 | 5 |
| 146 | 4 | 5 | 5 | 5 | 5 |
| 147 | 4 | 5 | 5 | 5 | 5 |
| 148 | 5 | 5 | 5 | 5 | 5 |
| 149 | 4 | 5 | 5 | 5 | 5 |
| 150 | 5 | 5 | 5 | 5 | 5 |
| 152 | 4 | 5 | 5 | 5 | 5 |
| 156 | 5 | 5 | 5 | 5 | 5 |
| 160 | 5 | 5 | 5 | 5 | 5 |
| 161 | 5 | 5 | 5 | 5 | 5 |
| 162 | 5 | 5 | 5 | 5 | 5 |
| 208 | 5 | 5 | 5 | 5 | 5 |
| 228 | 5 | 5 | 5 | 5 | 5 |
| 229 | 5 | 5 | 5 | 5 | 5 |
| 244 | 5 | 5 | 5 | 5 | 5 |
| 245 | 5 | 5 | 5 | 5 | 5 |
| 246 | 5 | 5 | 5 | 5 | 5 |
| 272 | 5 | 5 | 5 | 5 | 5 |
| 273 | 5 | 5 | 5 | 5 | 5 |

TEST EXAMPLE 2

(Test on herbicidal effects by upland field soil treatment)

Plastic pots of 120 cm² were filled with upland field soil. Seeds of barnyardgrass (Ec), pale smartweed (Po), slender amaranth (Am), common lambsquater (Ch) and rice flatsedge (Ci) were sown in the pots and covered with soil. Wettable powders prepared in accordance with Formulation Example 1 were diluted with water and applied uniformly to the soil surfaces by a small-sized sprayer in an amount of 100 ℓ/10 ares so as to apply 100 g of the active ingredient per 10 ares. The plants were then cultured in a green house, and the evaluation of the herbicidal effects was conducted on the 21st day after the application in accordance with the standards as identified in Table 6. The results are shown in Table 8.

TEST EXAMPLE 3

(Test on herbicidal effects by upland field foliage treatment)

Plastic pots of 120 cm² were filled with upland field soil. Seeds of barnyardgrass (Ec), pale smartweed (Po), slender amaranth (Am), common lambsquater (Ch) and rice flatsedge (Ci) were sown in the pots and covered with soil. Then the plants were cultured in a green house for 2 weeks. Wettable powders prepared in accordance with Formulation Example 1 were diluted with water and applied onto the entire foliages of the plants from above by a small-sized sprayer in an amount of 100 ℓ/10 ares so as to apply 100 g of the active ingredient per 10 ares. The plants were then cultured in the green house, and the evaluation of the herbicidal effects was conducted on the 14th day after the treatment in accordance with the standards as identified in Table 6. The results are shown in Table 9.

TABLE 9

| Compound No. | Herbicidal effects | | | | |
|---|---|---|---|---|---|
| | Ec | Po | Am | Ch | Ci |
| 1 | 5 | 5 | 5 | 5 | 5 |
| 2 | 5 | 5 | 5 | 5 | 5 |
| 23 | 5 | 5 | 5 | 5 | 5 |
| 37 | 5 | 5 | 5 | 5 | 5 |
| 38 | 5 | 5 | 5 | 5 | 5 |
| 60 | 5 | 5 | 5 | 5 | 5 |
| 61 | 5 | 5 | 5 | 5 | 5 |
| 62 | 5 | 5 | 5 | 5 | 5 |
| 77 | 5 | 5 | 5 | 5 | 5 |
| 95 | 5 | 5 | 5 | 5 | 5 |
| 98 | 5 | 5 | 5 | 5 | 5 |
| 99 | 5 | 5 | 5 | 5 | 5 |
| 100 | 5 | 5 | 5 | 5 | 5 |
| 102 | 4 | 5 | 5 | 5 | 5 |
| 104 | 4 | 5 | 5 | 4 | 5 |
| 105 | 5 | 5 | 5 | 5 | 5 |
| 106 | 5 | 5 | 5 | 5 | 5 |
| 107 | 5 | 5 | 5 | 5 | 5 |
| 108 | 5 | 5 | 5 | 5 | 5 |
| 112 | 5 | 5 | 5 | 5 | 5 |
| 135 | 5 | 5 | 5 | 5 | 5 |
| 136 | 5 | 5 | 5 | 5 | 5 |
| 137 | 4 | 5 | 5 | 5 | 5 |
| 138 | 5 | 5 | 5 | 5 | 5 |
| 144 | 5 | 5 | 5 | 5 | 5 |
| 145 | 4 | 5 | 5 | 4 | 5 |
| 146 | 4 | 5 | 5 | 5 | 5 |
| 147 | 4 | 5 | 5 | 5 | 5 |
| 148 | 4 | 5 | 5 | 5 | 5 |
| 149 | 4 | 5 | 5 | 5 | 5 |
| 150 | 4 | 5 | 5 | 5 | 5 |
| 151 | 4 | 5 | 5 | 5 | 5 |
| 152 | 5 | 5 | 5 | 5 | 5 |
| 156 | 4 | 5 | 5 | 4 | 5 |
| 160 | 5 | 5 | 5 | 5 | 5 |
| 161 | 5 | 5 | 5 | 5 | 5 |
| 162 | 5 | 5 | 5 | 5 | 5 |
| 171 | 4 | 5 | 5 | 5 | 5 |
| 208 | 5 | 5 | 5 | 5 | 5 |
| 209 | 5 | 5 | 5 | 5 | 5 |
| 228 | 5 | 5 | 5 | 5 | 5 |
| 229 | 5 | 5 | 5 | 5 | 5 |
| 244 | 5 | 5 | 5 | 5 | 5 |
| 245 | 5 | 5 | 5 | 5 | 5 |
| 246 | 5 | 5 | 5 | 5 | 5 |
| 272 | 5 | 5 | 5 | 5 | 5 |
| 279 | 5 | 5 | 5 | 5 | 5 |

TEST EXAMPLE 4

(Test on crop plant selectivity by upland field soil treatment)

Plastic pots of 600 cm² were filled with upland field soil. Seeds of wheat (Tr), blackgrass (Al), pale smartweed (Po), slender amaranth (Am) and common lambsquater (Ch) were sown in the pots and covered with soil. Next day, wettable powders containing prescribed amounts of the active ingredients (ai,g/10a) prepared in accordance with Formulation Example 1 were diluted with water and applied uniformly to the soil surfaces by a small-sized sprayer in an amount of 100 ℓ per 10 ares. The plants were then cultured in a green house, and the evaluation of the herbicidal effects was conducted on the 21st day after the application in accordance with the standards as identified in Table 6. The results, inclusive of those for comparative compounds, are shown in Table 10.

TABLE 10

| Compound No. | Dose $g^{ai}/10a$ | Herbicidal effects | | | | Phytotoxicity |
|---|---|---|---|---|---|---|
| | | Al | Po | Am | Ch | Tr |
| 60 | 1.6 | 5 | 5 | 5 | 3 | 0 |
| 62 | 0.4 | 4 | 5 | 5 | 5 | 0 |
| 95 | 0.4 | 5 | 5 | 5 | 5 | 1 |
| 98 | 6.3 | 5 | 5 | 5 | 5 | 1 |
| 99 | 1.6 | 5 | 5 | 5 | 5 | 0 |
| 100 | 6.3 | 5 | 5 | 5 | 5 | 1 |
| 101 | 6.3 | 5 | 5 | 5 | 5 | 0 |
| 103 | 6.3 | 4 | 5 | 5 | 5 | 0 |
| 272 | 6.3 | 5 | 5 | 5 | 5 | 0 |
| 244 | 0.4 | 4 | 5 | 5 | 3 | 0 |
| *1 | 1.6 | 5 | 5 | 5 | 5 | 3 |
| *2 | 6.3 | 3 | 4 | 4 | 5 | 2 |
| *3 | 6.3 | 1 | 4 | 4 | 5 | 1 |
| *4 | 6.3 | 1 | 4 | 4 | 5 | 1 |

*1 Comparative Compound A: Methyl 2-chloro-6-(4,6-dimethoxypyrmidin-2-yl)carbonyl benzoate (Compound No. 55 of EP0461079)
*2 Comparative Compound B: 2-(4,6-Dimethoxypyrimidin-2-yl)methyl nicotinic acid (Compound No. 6 of WO91/10653, Compound No. 1 of DE4026177)
*3 Comparative Compound C: 7-(4,6-Dimethoxypyrimidin-2-yl)-7-hydroxy-furol[3,4-b]pyridin-5(7H)one (Compound No. 175 of EP0461079)
*4 Comparative Compound D: 2-(4,6-Dimethoxypyrimidin-2-yl)carbonyl nicotinate (Compound No. 176 of EP0461079)

TEST EXAMPLE 5

(Test on crop plant selectivity by upland field foliage treatment)

Plastic pots of 600 cm² were filled with upland field soil. Seeds of wheat (Tr), blackgrass (Al), pale smartweed (Po), slender amaranth (Am) and common lambsquater (Ch) were sown in the pots, and the plants were cultured in a greenhouse for 2 weeks. Wettable powders containing prescribed amounts of the active ingredients (ai,g/10a) prepared in accordance with Formulation Example 1 were diluted with water and applied onto the entire foliages of the plants from above by a small-sized sprayer in an amount of 100 ℓ/10 ares. The plants were then cultured in the green house, and the evaluation of the herbicidal effects was conducted on the 14th day after the treatment in accordance with the standards as identified in Table 6. The results, inclusive of those for comparative compounds, are shown in Table 11.

TABLE 11

| Compound No. | Dose $g^{ai}/10a$ | Herbicidal effects | | | | Phytotoxicity |
|---|---|---|---|---|---|---|
| | | Al | Po | Am | Ch | Tr |
| 98 | 6.3 | 5 | 5 | 5 | 5 | 0 |
| 99 | 6.3 | 5 | 5 | 5 | 4 | 0 |
| 105 | 0.4 | 5 | 5 | 5 | 4 | 0 |
| 106 | 0.4 | 5 | 5 | 5 | 4 | 0 |
| 272 | 25 | 5 | 5 | 5 | 5 | 0 |
| 244 | 0.4 | 5 | 5 | 4 | 3 | 0 |
| *3 | 25 | 1 | 5 | 5 | 5 | 4 |
| | 6.3 | 1 | 4 | 5 | 4 | 3 |
| *4 | 25 | 2 | 5 | 5 | 5 | 4 |
| | 6.3 | 1 | 4 | 5 | 5 | 3 |
| *5 | 25 | 3 | 5 | 4 | 4 | 2 |

*5) Comparative Compound E: Ethyl 2-[α-cyano-(4,6-dimethoxypyrimidin-2-yl)]methyl nicotinate (Compound No. 142 of EP0461079)

We claim:
1. A nicotinic acid derivative represented by the formula

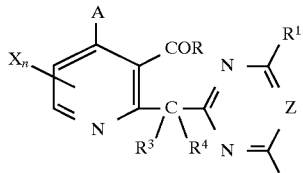

or

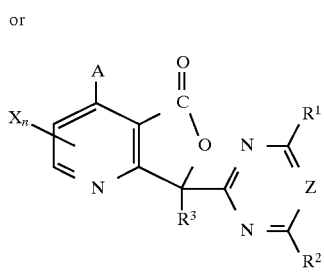

wherein A is one of the groups of the formulae

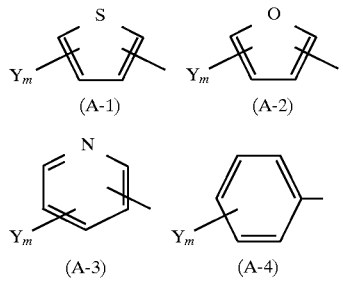

(wherein Y is a halogen atom, a hydroxyl group, an optionally substituted alkoxy group, an alkenyloxy group, an alkynyloxy group, an optionally halogen-substituted alkyl group, an acyloxy group, a benzyloxy group or a nitro group, and m is 0 or an integer of from 1 to 3, provided that when m is 2 or 3, each Y may be a different group), R is a hydroxyl group, an optionally substituted alkoxy group, an optionally substituted benzyloxy group, an alkenyloxy group, an alkynyloxy group, an optionally substituted phenoxy group, an optionally substituted phenylthio group, an alkylthio group, a 1-imidazolyl group, an isopropylideneaminoxy group or a group represented by the formula —$NR^5R^6$ (wherein each of $R^5$ and $R^6$ which may be the same or different, is a hydrogen atom, an alkyl group, an optionally substituted phenyl group, an alkylsulfonyl group or an optionally substituted phenylsulfonyl group, or $R^5$ and $R^6$ may form a ring together with the nitrogen atom) or the formula —$ONR^5R^6$ (wherein $R^5$ and $R^6$ are as defined above), each of $R^1$ and $R^2$ which may be the same or different, is a hydrogen atom, an alkoxy group, a halogen atom, an alkylamino group, a dialkylamino group, a halogen-substituted alkoxy group or an alkyl group, each of $R^3$ and $R^4$ which may be the same or different, is a hydrogen atom, a hydroxyl group, a cyano group or an alkoxycarbonyl group, or $R^3$ and $R^4$ may together represent an oxygen atom in combination, X is a halogen atom, an alkyl group, an alkoxy group, an amino group, an alkylamino group, a dialkylamino group or an acylamino group, n is 0 or an integer of from 1 to 2, provided that when n is 2, each X may be a different group, and Z is a methine group; or a salt thereof; wherein the substituents on said optionally substituted alkoxy group are alkoxy, halogen, or haloalkoxy, and wherein the substituents on said optionally substituted benzyloxy group, said optionally substituted phenoxy group, and said optionally substituted phenylthio group are independently selected from the group consisting of halogen, alkyl, alkoxy, nitro, and cyano, and wherein the substituents on said optionally substituted phenyl group or said optionally substituted phenyl sulfonyl group are independently selected from the group consisting of halogen, alkyl, alkoxy, and nitro.

2. A nicotinic acid derivative represented by the formula

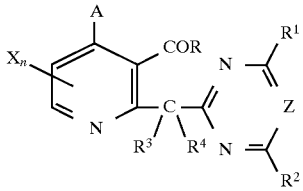

or

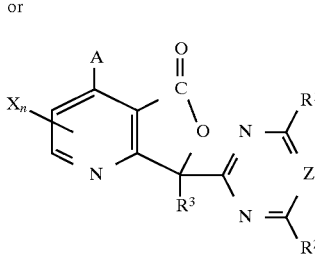

wherein A is one of the groups of the formulae

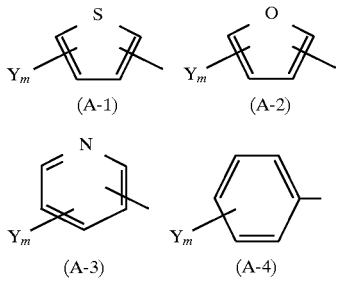

(wherein Y is a halogen atom, an alkyl group, an alkoxy group or a nitro group, and m is 0 or an integer of from 1 to 2, provided that when m is 2, each Y may be a different group), R is a hydroxyl group, an optionally substituted alkoxy group, an optionally substituted benzyloxy group, an alkenyloxy group, an alkylthio group, an isopropylideneaminoxy group, a 1-imidazolyl group, a group represented by the formula —$NR^5R^6$ (wherein each of $R^5$ and $R^6$ is an alkyl group) or the formula —$ONR^5R^6$ (wherein $R^5$ and $R^6$ are as defined above), each of $R^1$ and $R^2$ is an alkoxy group, each of $R^3$ and $R^4$ which may be the same or different, is a hydrogen atom, a hydroxyl group, a cyano group or an alkoxycarbonyl group, or $R^3$ and $R^4$ may together represent an oxygen atom, X is an alkyl group, n is 0 or an integer of 1, and Z is a methine group; or a salt thereof, wherein the substituents on said optionally substituted alkoxy group are alkoxy, halogen, or haloalkoxy, and wherein the substituents on said optionally substituted benzyloxy group are selected from the group consisting of halogen, alkyl, alkoxy, nitro, and cyano.

3. The compound according to claim 1, wherein A in the formula (I) or (II) represents the formula (A-1) or the formula (A-2).

4. The compound according to claim 2, wherein A in the formula (I) or (II) represents the formula (A-1) or the formula (A-2).

5. The compound according to claim 1, wherein A in the formula (I) or (II) represents the formula (A-3).

6. The compound according to claim 2, wherein A in the formula (I) or (II) represents the formula (A-3).

7. The compound according to claim 1, wherein A in the formula (I) or (II) represents the formula (A-4).

8. The compound according to claim 2, wherein A in the formula (I) or (II) represents the formula (A-4).

9. A nicotinic acid derivative represented by the formula

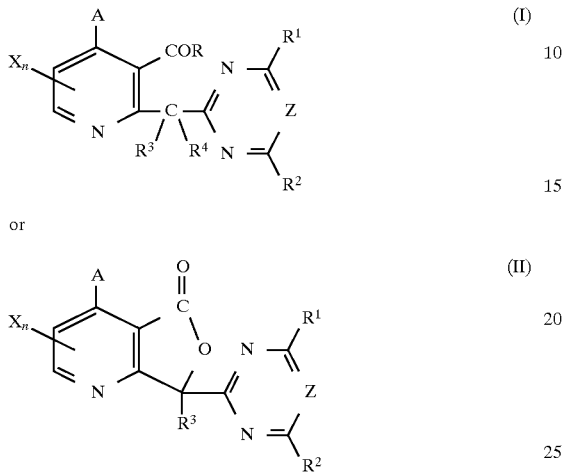

wherein A is a phenyl group which may be substituted with one or two halogen atoms, alkyl groups or alkoxy groups, R is a hydroxyl group, an alkoxy group which may be substituted with a halogen atom or with an alkoxy group, an alkylthio group, a benzyloxy group which may be substituted with a halogen atom, an alkyloxy group, a dialkylamino group or a dialkylaminoxy group, each of $R^1$ and $R^2$ is a methoxy group, $R^3$ in the formula (I) is a cyano group, $R^3$ in the formula (II) is a hydroxyl group or a cyano group, $R^4$ is a hydrogen atom, or $R^3$ and $R^4$ may together represent an oxygen atom, n is 0, and Z is a methine group; or a salt thereof.

10. A process for producing a compound as defined in claim 1, which comprises reacting a compound represented by the formula (a),

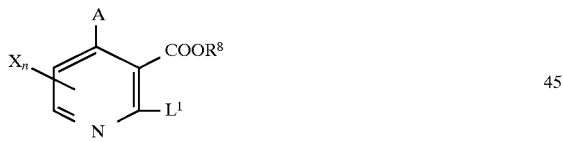

wherein A is one of the groups of the formulae

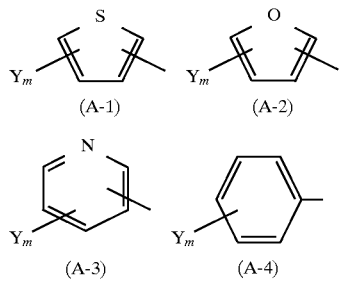

(wherein Y is a halogen atom, a hydroxyl group, an optionally substituted alkoxy group, an alkenyloxy group, an alkynyloxy group, an optionally halogen-substituted alkyl group, an acyloxy group, a benzyloxy group or a nitro group, and m is 0 or an integer of from 1 to 3, provided that when m is 2 or 3, each Y may be a different group), $R^8$ is an aikyl group, X is a halogen atom, an alkyl group, an alkoxy group, an amino group, an alkylamino group, a dialkylamino group or an acylamino group, n is 0 or an integer of from 1 to 2, provided that when n is 2, each X may be a different group, and $L^1$ is a halogen atom, with a compound represented by the formula (b),

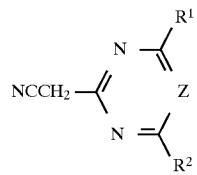

(wherein each of $R^1$ and $R^2$ which may be the same or different and is a hydrogen atom, an alkoxy group, a halogen atom, an alkylamino group, a dialkylamino group, a halogen-substituted alkoxy group or an alkyl group, and Z is a methine group in the presence of at least twice the equivalent amount of a base in a solvent, followed by acidification to give a compound represented by the general formula (c),

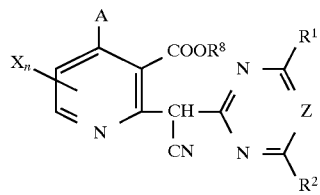

reacting the formula (c) with an organic peroxide in a solvent to give a compound represented by the formula (d),

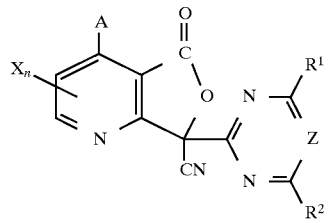

(wherein A, $X_n$, $R^1$, $R^2$ or Z is as defined above), reacting the compound represented by the formula (d) in the presence of a base in water or a hydrous solvent, followed by acidification to give a compound represented by the formula (e).

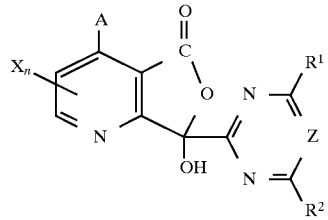

(wherein A, $X_n$, $R^1$, $R^2$ or Z is as defined above), and either reacting the compound represented by the formula (e) with a compound represented by the formula (f),

R$^{10}$L$^1$ (wherein R$^{10}$ is an optionally substituted alkyl group, an optionally substituted benzyl group, an alkenyl group, an alkynyl group, and L$^1$ is a halogen atom) to give a compound represented by the formula (g),

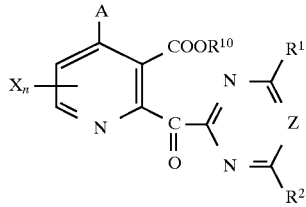

(wherein A, X$_n$, R$^1$, R$^2$, R$^{10}$, and Z is as defined above), or reacting the compound represented by the formula (e) with a compound represented by the formula (h),

RH (wherein R is as defined in claim 1) in the presence of a condensation agent in a solvent to give a compound represented by the formula (i),

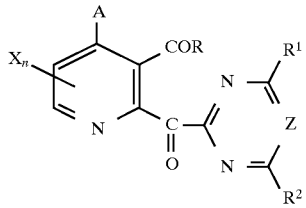

(wherein A, X$_n$, R, R$^1$, R$^2$ or Z is as defined above); wherein the substituents on said optionally substituted alkoxy group are alkoxy, halogen, or haloalkoxy, and wherein the substituents on said optionally substituted benzyloxy group, said optionally substituted phenoxy group, and said optionally substituted phenylthio group are independently selected from the group consisting of halogen, alkyl, alkoxy, nitro, and cyano, and wherein the substituents on said optionally substituted phenyl group or said optionally substituted phenyl sulfonyl group are independently selected from the group consisting of halogen, alkyl, alkoxy, and nitro.

11. A herbicide composition comprising the nicotinic acid derivative or a salt thereof according to claim 1, as an active ingredient, and a carrier.

12. A herbicide composition comprising the nicotinic acid derivative or a salt thereof according to claim 9, as an active ingredient, and a carrier.

13. A process for producing a nicotinic acid derivative, comprising: reacting a compound having the formula (a)

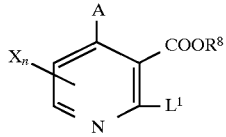

(a)

wherein A is one of the groups having the formula:

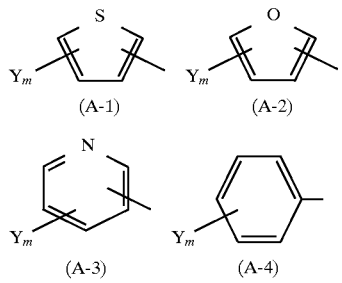

(A-1)  (A-2)

(A-3)  (A-4)

wherein Y is a halogen atom, a hydroxyl group, an optionally substituted alkoxy group, an alkenyloxy group, an alkynyloxy group, an optionally halogen-substituted alkyl group, an acyloxy group, a benzyloxy group or a nitro group, and m is 0 or an integer of from 1 to 3, provided that when m is 2 or 3, each Y may be a different group, R$^8$ is an alkyl group, X is a halogen atom, an alkyl group, an alkoxy group, an amino group, an alkylamino group, a dialkylamino group or an acylamino group, n is 0 or an integer of from 1 to 2, provided that when n is 2, each X may be a different group, and L$^1$ is a halogen atom;

with a compound having the formula (b):

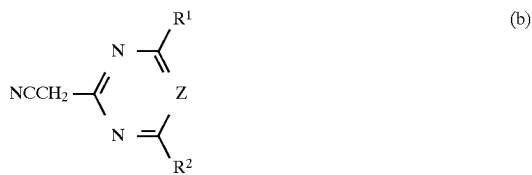

(b)

wherein each of R$^1$ and R$^2$ is independently a hydrogen atom, an alkoxy group, a halogen atom, an alkylamino group, a dialkylamino group, a halogen-substituted alkoxy group or an alkyl group, and Z is a methine group;

in the presence of at least twice the equivalent amount of a base in a solvent, followed by acidification to give a compound having the general formula (e):

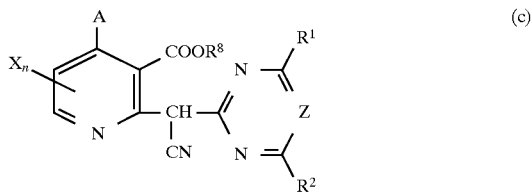

(c)

wherein the substituent on said optionally substituted alkoxy group is alkoxy, halogen, or haloalkoxy.

14. The process of claim 10, wherein the compound represented by the formula (e) is reacted with a compound represented by the formula (f).

15. The process of claim 10, wherein the compound represented by the formula (e) is reacted with a compound represented by the formula (h).

* * * * *